(12) United States Patent
Mulet Salort et al.

(10) Patent No.: US 7,612,177 B2
(45) Date of Patent: Nov. 3, 2009

(54) PROTEIN FOR USE IN MODIFYING ABIOTIC STRESS TOLERANCE IN YEAST

(75) Inventors: Jose Miguel Mulet Salort, Basel (CH); Ramon Serrano Salom, Valencia (ES)

(73) Assignee: Cropdesign N.V., Zwijnaarde (BE)

( * ) Notice: Subject to any disclaimer, the term of this patent is extended or adjusted under 35 U.S.C. 154(b) by 292 days.

(21) Appl. No.: 10/552,686

(22) PCT Filed: Apr. 13, 2004

(86) PCT No.: PCT/EP2004/050513

§ 371 (c)(1),
(2), (4) Date: Nov. 21, 2005

(87) PCT Pub. No.: WO2004/090141

PCT Pub. Date: Oct. 21, 2004

(65) Prior Publication Data

US 2006/0200879 A1   Sep. 7, 2006

(30) Foreign Application Priority Data

Apr. 11, 2003   (EP)   .................... 03076064

(51) Int. Cl.
*C07K 14/415* (2006.01)
*C12N 15/81* (2006.01)
(52) U.S. Cl. ..................... 530/370; 435/483
(58) Field of Classification Search ........... None
See application file for complete search history.

(56) References Cited

FOREIGN PATENT DOCUMENTS

WO   WO 00/08187   2/2000
WO   WO 02/052012   * 7/2002

OTHER PUBLICATIONS

Broun P et al. Catalytic plasticity of fatty acid modification enzymes underlying chemical diversity of plant lipids. Science. Nov. 13, 1998;282(5392):1315-7.*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov 13, 1998;273(46):30750-6.*
Bevan M. et al. Putative uncharacterized protein F19B15.190 (At4g29160), Uniprot Accession No. Q9SZE4, May 1, 2000.*
International Search Report for PCT/EP2004/050513 dated Mar. 1, 2005.
Jeong et al., *Isolation and characterization of the gene encoding glyceraldehydes-3-phosphate dehydrogenase*, Biochemical and Biophysical Research Communications, Nov. 11, 2000, vol. 278, No. 1, pp. 192-196, XP002255015.
Kim et al., *A novel cold-inducible zinc finger protein from soybean, SCOF-1, enhances cold tolerance in transgenic plants*, Plant Journal, Feb. 2001, vol. 25, No. 3, pp. 247-259, XP002973197.
Rodriguez-Vargas et al., *Gene expression analysis of cold and freeze stress in baker's yeast*, Applied and Environmental Microbiology, Jun. 2002, vol. 68, No. 6, pp. 3024-3030, XP002304505.
Howard Tiffani et al., *CHMP1 functions as a member of a newly defined family of vesicle trafficking proteins*, Journal of Cell Science, Jul. 2001, vol. 114, No. 13, pp. 2395-2404, XP002304506.

* cited by examiner

*Primary Examiner*—Cynthia Collins
(74) *Attorney, Agent, or Firm*—Nixon & Vanderhye P.C.

(57) ABSTRACT

A method is presented for selecting and isolating nucleic acids capable of conferring tolerance or resistance to environmental stress conditions in plants or yeast. Furthermore, nucleic acids, the proteins they encode and their use for the production of plants or yeast with enhanced environmental stress resistance is disclosed.

13 Claims, 5 Drawing Sheets

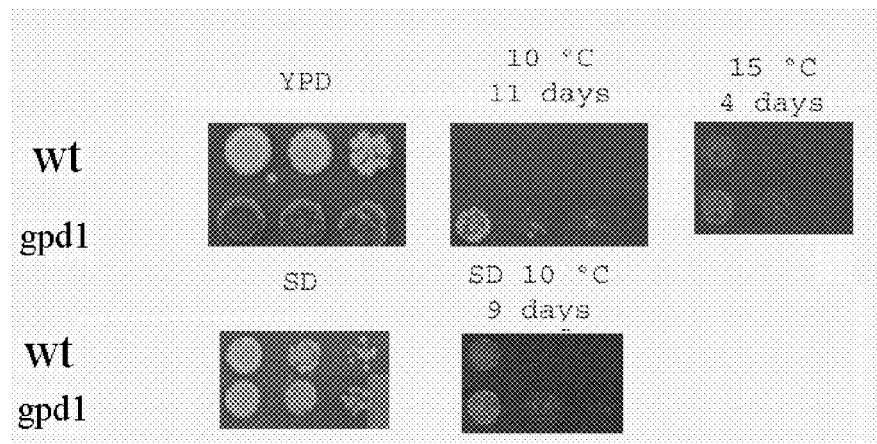
FIGURE 1
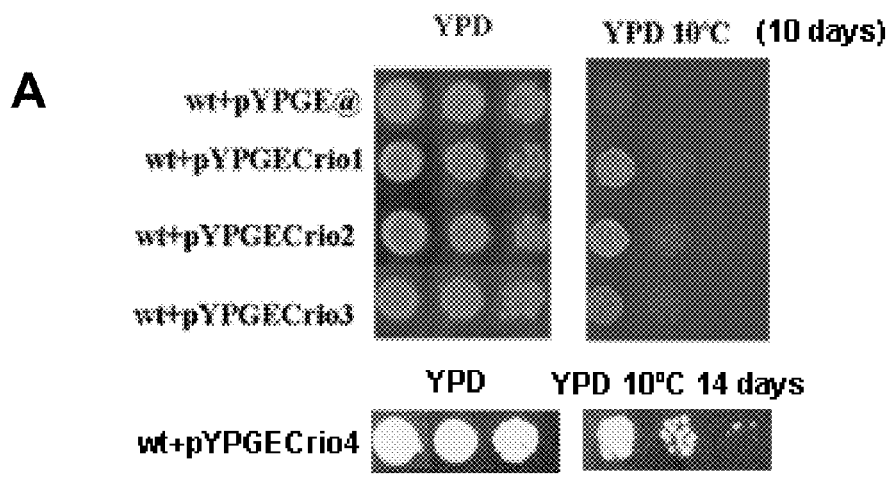
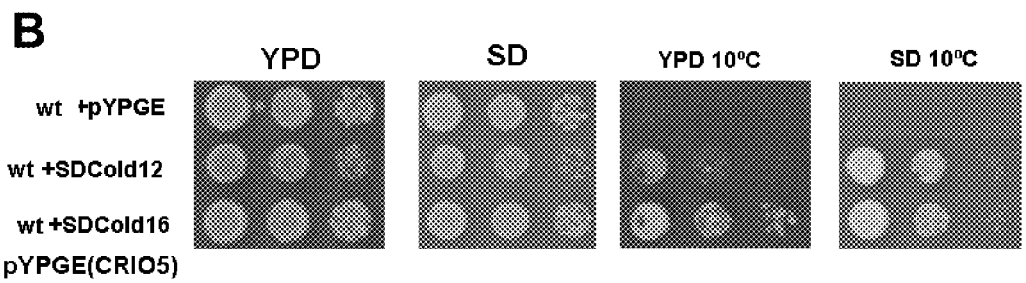
FIGURE 2

```
         1                                                            50
AtCRYO1  ~MMNRLFG.K  PKQ.EA..NA  LQTLDKLNET  LEMLEKKEKV  LLKKAGAEVE
AtCRYO2  MFMNRLFG.K  PKQ.ET..ST  LQTLDKLNET  LEMLEKKENV  LLKKATGEVE
BvCRYO2  ~MFTRVFG.K  PKEGTT..SA  VATLDKLSET  LEMLEKKEQV  LLKKAGAEVE
BvCRYO1  ~MFSRLFGAK  SRDAATTETT  LSTLEKLNET  LEMLEKKEQL  LMKKATAEVE
 scdid1  ~MWSSLFGWT  SSNAKNKESP  TKAIVRLREH  INLLSKKQSH  LRTQITNQEN 51                                                           100
AtCRYO1  KAKEYSRAKN  KRAAIQCLKR  KRLYEGQVEQ  LGNFQLRIHD  QMIMLEGAKA
AtCRYO2  KAKEFSRAKN  KRAAIQCLKR  KRLYEQQVEQ  LGNFQLRIHD  QMIMLEGAKA
BvCRYO2  KAKEFTRAKN  KRAAITCLKR  KRLYEQQIEQ  LGNMQLRIHD  QMILLEGAKA
BvCRYO1  KAKEFTRAKN  KRAAIQCLKR  KRLYEQQVEQ  VGNFQLRIHD  QIIMLDSAKA
 Scdid1  EARIFLTKGN  KVMAKNALKK  KKTIEQLLSK  VEGTMESMEQ  QLFSIESANL 101                                                          150
AtCRYO1  TTETVDALRS  GASAMKAMQK  A.TNIDDVDK  TMDEINEQTE  NMKQIQEALA
AtCRYO2  TTETVDALRT  GASAMKAMQK  A.TNIDDVDK  TMDEINEQTE  NMKQIQEALS
BvCRYO2  TTETVDALRS  GASAMKAMQK  A TNIDNVDK   TMDEIENQTE  NLKQIQEALSAPIGAAD
BVCRYO1  TTETVAALRS  GASAMKAMQK  A.TNIDDVDK  TMDEINEQTD  NLRQIRRH
 Scdid1  NLETMRAMQE  GAKAMKTIH.  SGLDIDKVDE  TMDEIREQVE  LGDEISDAIS
```

FIGURE 3

```
                1                                                               50
AtCRYO3.2 ~~MGNTDKLM  NQIFELKFTS  KSLQRQARKC  EKEERSEKLK  VKKAIEKGNM
AtCRYO3.1 ~~MGNTDKLM  NQIFELKFTS  KSLQRQARKC  EKEERSEKLK  VKKAIEKGNM
  AtCRYO3 ~~MGNTDKLM  NQIFDLKFTS  KSLQRQSRKC  EKEEKAEKLK  VKKAIEKGNM
  BvCRYO3 ~~MGNTEKLM  NQIMELKFTS  KSLQRQSRKC  EKEEKAEKLK  VKKAIEKGNM
  DeCRYO3 ~~~~~~~~ME  NQLFQLKFTS  KQLEKQSKKS  EQSEKAQKIK  LKKAIEQGNM
  MmCRYO3 ~~~~~~~~MD  DTLFQLKFTA  KQLEKLAKKA  EKDSKAEQAK  VKKALQQKNV
  HsCRYO3 ~~~~~~~~MD  DTLFQLKFTA  KQLEKLAKKA  EKDSKAEQAK  VKKALLQKNV
  ScCRYO3 MSRNSAAGLE  NTLFQLKFTS  KQLQKQANKA  SKEEKQETNK  LKRAL.NENE
  SpCRYO3 ~~~~~~~~~~  ~~~~~~~~~~  ~~~~~~~MSL  SMNFFTAHLS  IAIAITKGNS 51                                                              100
AtCRYO3.2 DGARIYAENA  IRKRSEQMNY  LRLSSRLDAV  VARLDTQAKM  ATITKSMTNI
AtCRYO3.1 DGARIYAENA  IRKRSEQMNY  LRLSSRLDAV  VARLDTQAKM  ATITKSMTNI
  AtCRYO3 DGARIYAENA  IRKRSEQMNY  LRLASRLDAV  VARLDTQAKM  TTITKSMTNI
  BvCRYO3 DGARIYAENA  IRKRTEQMNY  LRLASRLDAV  VSRLDTQAKM  QTIGKSMGSI
  DeCRYO3 DGARIYAQNA  IREKNQSLNY  LRLASRIDAV  ASRVETAIRM  KSVTGSMANI
  MmCRYO3 ECARVYAENA  IRKKNEGVNW  LRMASRVDAV  ASKVQTAVTM  KGVTKNMAQV
  HsCRYO3 ECARVYAENA  IRKKNEGVNW  LRMASRVDAV  ASKVQTAVTM  KGVTKNMAQV
  ScCRYO3 DISRIYASNA  IRKKNERLQL  LKLASRVDSV  ASRVQTAVTM  RQVSASMGQV
  SpCRYO3 EIARIYASNA  IRKQQESLNL  LKLSSRIDAV  SSRLQTAVTM  RAVSGNMAGV 101                                                             150
AtCRYO3.2 VKSLESSLTT  GNLQKMSETM  DSFEKQFVNM  EVQAEFMDNA  MAGSTSLSTP
AtCRYO3.1 VKSLESSLTT  GNLQKMSETM  DSFEKQFVNM  EVQAEFMDNA  MAGSTSLSTP
  AtCRYO3 VKSLESSLAT  GNLQKMSETM  DSFEKQFVNM  EVQAEFMENA  MAGSTSLSTP
  BvCRYO3 VKSLESSLNT  GNLQKMSETM  DNFEKQFVNM  EVQAEFMESS  MAGSTSLSTP
   DeDID2 VKSMEKSMRN  MDLEKITQVM  DQFERQFEDL  DVQSVYVENA  MNQTTTLSTP
   MmDID2 TKALDKALSA  MDLQKVSAVM  DRFEQQVQNL  DVHTSVMEDS  VSSATTLTTP
   HsDID2 TKALDKALST  MDLQKVSSVM  DRFEQQVQNL  DVHTSVMEDS  MSSATTLTTP
   ScDID2 CKGMDKALQN  MNLQQITMIM  DKFEQQFEDL  DTSVNVYEDM  GVNSDAMLVD
   SpDID2 VRGMDRAMKT  MNLEMISQVM  DKFEAQFDDV  NVQTGYMNKA  MGSVTAVDTP 151                                                             200
AtCRYO3.2 EGEVNSLMQQ  VADDYGLEV.  .SVGLPQ.PA  GHAIPTKTEE  KVEEDDLTRR
AtCRYO3.1 EGEVNSLMQQ  VADDYGLEV.  .SVGLPQ.PA  GHAIPTKTEE  KVEEDDLTRR
  AtCRYO3 EGEVNSLMQQ  VADDYGLEV.  .SVGLPQ.PA  GHAIPTKTEE  KVDEDDLSRR
  BvCRYO3 ETEVNSLMQQ  VADDYGLEG.  .SVGLPQ.AA  GHAIPV...P  KAAEKVDEG*
   DeDID2 ADQVDLLISQ  VADEHGL...  .NVGMQM...  GSA.PSEKVQ  QGETDELTER
   MmDID2 QEQVDSLIVQ  IAEENGLEVL  D..QLSQLPE  GASAVGESSV  RSQEDQLSRR
   HsDID2 QEQVDSLIMQ  IAEENGLEVL  D..QLSQLPE  GASAVGESSV  RSQEDQLSRR
   ScDID2 NDKVDELMSK  VADENGMELK  QSAKLDNVPE  .IKAKEVNVD  DEKEDKLAQR
   SpDID2 QEDVDLLMQT  VADEAGLEFN  QNMNNNLSVP  AASVPTPAAP  .VEDDNLQER
```

FIGURE 4

PROTEIN FOR USE IN MODIFYING ABIOTIC STRESS TOLERANCE IN YEAST

This application is the US national phase of international application PCT/AU2004/000465 filed 8 Apr. 2004, which designated the U.S. and claims priority to AU 2003901660 filed 8 Apr. 2003, the entire contents of each of which are hereby incorporated by reference.

FIELD OF THE INVENTION

The present invention concerns a method for identifying and obtaining nucleic acids capable of modifying stress tolerance, particularly cold tolerance, in plants. The invention also concerns isolated nucleic acids so obtained. The invention further concerns a method for obtaining plants having modified stress tolerance and to plants obtained by the methods according to the invention. The invention also relates to a yeast strain having modified tolerance to cold stress.

BACKGROUND

Environmental stress conditions, such as shortage or excess of solar energy, water or nutrients, high salinity and pollution (e.g., heavy-metal pollution), can have a major impact on plant growth and can significantly reduce plant yield. Osmotic stress, a type of environmental stress, may be induced by conditions of excess salinity, drought, excessive heat, cold or freezing.

Cold stress may be induced by temperatures below the range which allow optimal growth for a particular plant species. Each plant species or variety has an optimal growth temperature at which the growth rate is maximal; the further the deviation from this optimal growth temperature, the greater the stress on the plants. Many plant species, especially from tropical or subtropical regions, are sensitive to cold. For example, it has been estimated that the worldwide rice production would decrease by 40% if the worldwide mean temperature dropped only between 0.5 to 1.0° C. (Salisbury and Ross, Plant Physiology. 4*th* ed. Wadsworth Publishing Company, Belmont, Calif., 1992). Plants from temperate regions however have the ability to adapt their metabolism and to survive freezing temperatures after undergoing a process of adaptation to low but non-freezing temperatures, a process called cold acclimation. For instance non-acclimated rye typically does not survive temperatures below −5° C., but after cold acclimation it can withstand temperatures as low as −30° C. The process of cold acclimation involves altered expression of many genes. Plants may differ in their ability to withstand cold, which could lead to periodic but significant losses in plant productivity. As a consequence, the areas in which crops or horticultural plants can be cultivated is determined by assessing the risk of lower temperatures, relative to typical growth temperatures for any given plant.

The most prominent changes during cold acclimation include a reduction or cessation of growth, reduction of tissue water content (Levitt; Responses of Plants to Environmental Stresses, Vol. 1. 2nd edn. Academic Press. New York, N.Y. 1980), transient increase in abscisic acid (ABA) levels (Chen et al., Plant Physiology 71, 362-365, 1983), changes in membrane lipid composition (Lynch and Steponkus, Plant Physiology 83, 761-767, 1987; Uemura and Steponkus, Plant Physiology 104, 479-496, 1994), the accumulation of compatible osmolytes such as proline, betaine, polyols and soluble sugars, and increased levels of antioxidants (Koster and Lynch, Plant Physiology 98, 108-113, 1992; Kishitani et al., Plant, Cell and Environment 17, 89-95, 1994; Murelli et al., Physiologia Plantarum 94, 87-93 1995; Nomura et al., *Euphytica* 83, 247-250, 1995; Dorffling et al., Plant Molecular Biology 23, 221-225, 1997; Tao et al., Cryobiology 37, 38-45, 1998).

Various methods for the identification and isolation of genes or proteins differentially expressed during cold stress are known. For example, mapping techniques allow determination of chromosome locations of genes involved in cold tolerance (Pan et al., Theoretical and Applied Genetics 89, 900-910, 1994; Galiba et al., Theoretical and Applied Genetics 90, 1174-1179, 1995). Another approach involves mutational analysis in which mutants that have an altered response to cold tolerance are isolated and characterized. For example, eskimo1, conferring improved freezing tolerance of 2° C. over acclimated wild-type plants, was isolated from a collection of 800000 Ethyl Methyl Sulphonate (EMS)—mutagenised *Arabidopsis* lines that were screened for constitutively freezing-tolerant mutants (Xin and Browse, PNAS 95, 7799-7804, 1998). Conversely, plant lines were screened for mutants defective in cold acclimation (Warren et al., Plant Physiology 111, 1011-1019, 1996; Knight et al., Plant Cell 8, 489-503, 1996). cos-, los- and hos-mutants (for respectively constitutive, low and high expression of osmotically responsive genes) were isolated using a combination of mutagenesis and reporter gene activation (Ishitani et al., Plant Cell 9, 1935-1949, 1997; Ishitani et al., Plant Cell 10, 1151-1161, 1998; Lee et al., Plant Journal 17, 301-308, 1999). One of the drawbacks of mapping and the mutant analysis strategy is that they do not directly result in the isolation of nucleic acids coding for cold-induced genes. Another strategy, using differential screening of cDNA libraries and related techniques, has in the past yielded several cold induced genes from different plant species (reviewed in Xin and Browse, Plant, Cell and environment 23, 893-902, 2000). Many of those genes have known functions and can be grouped as being involved in drought stress, in signal transduction pathways, or as being related to heat shock proteins, molecular chaperones, "antifreeze proteins" or regulatory proteins. Several of the genes are highly expressed during cold stress and are commonly referred to as COR (COld Regulated) genes (Tomashow, Annual Review of Plant Physiology and Plant Molecular Biology 50, 571-599, 1999).

Strategies used to engineer cold resistant plants include accumulation of osmoprotectants such as mannitol (U.S. Pat. No. 6,416,985), proline (U.S. Pat. No. 6,239,332), trehalose (U.S. Pat. No. 6,323,001) or glycine-betaine (Hayashi et al., Plant Journal 12, 133-142, 1997; U.S. Pat. No. 6,281,411). Other approaches involve manipulating the signal transduction pathway controlling the stress response (WO 01/77355), including use of transcription factors (WO 01/77311, U.S. Pat. No. 6,417,428, WO 02/44389, U.S. Pat. No. 5,891,859). Furthermore a number of genes have been used to enhance cold resistance. Examples are members of the COR group (COR15a: U.S. Pat. No. 5,296,462, U.S. Pat. No. 5,356,816), a cell cycle related gene (WO 01/77354), protein kinase related proteins (WO 01/77356), the LEA-like protein CAP85 (U.S. Pat. No. 5,837,545) and use of a phospholipid binding protein (WO 02/00697). Nevertheless, signal transduction pathways leading to cold acclimation and the identity of the genes that confer resistance to cold stress in plants remain largely unknown.

Yeast has been used for screening plant genes that confer resistance to salt stress. For example, a salt-sensitive yeast strain (JM26) has previously been transformed with a cDNA library from salt-stressed sugar beet and used to screen for clones having increased salt tolerance (WO 02/52012). The transformed yeast cells were grown on a rich medium (YPD)

or on a synthetic medium plus methionine and leucine (SD), supplemented with 0.15 M NaCl or with 20 mM LiCl. Putative positive clones showing better growth on the selective media compared to the non-transformed yeast strain were isolated and further characterised. However, the use of yeast for identifying plant genes involved in cold stress has not been used before. A recent study in haploid yeast by de Jesus Ferreira et al. (2001), in which transposon mutagenesis was employed, identified 10 different yeast genes responsive to cold tolerance, which upon mutation caused a growth stop at 15° C. The identified genes include a gene coding for a glutamate synthase (YDL171C), a GTP binding protein (YML121W), a GSK-3 Ser/Thr protein kinase (YNL307C) and a component of TFIID (YLR399C). Three of the genes were previously described as cold responsive (YLR399c, YML121W, YNL307C) and four of the isolated genes were also involved in resistance to salt stress.

SUMMARY OF THE INVENTION

The present invention provides a novel screening method for nucleic acids involved in stress responses in a plant, which method involves screening in diploid yeast for plant genes involved in modifying tolerance/resistance to temperature stress. The present invention also provides new plant genes identified by this screen and polypeptides encoded by these genes. Also provided are methods for producing plants having modified tolerance or resistance to environmental stress conditions, comprising introduction of the above-mentioned genes into plants. Also provided are plants having modified tolerance or resistance to environmental stress conditions, which plants are transformed with the gene according to the invention.

DETAILED DESCRIPTION OF THE INVENTION

According to a first embodiment of the present invention, there is provided a screening method for identifying nucleic acids capable of modifying tolerance or resistance to cold stress conditions in plants or yeast, which method comprises the steps of:
  (i) providing a cDNA library of coding sequences from an organism;
  (ii) introducing these coding sequences in an expressible format into wild type yeast cells;
  (iii) growing the yeast cells of (ii) under conditions of cold stress;
  (iv) identifying differences between transgenic yeast cells and wild type yeast cells, preferably identifying differences in growth rate;
  (v) isolating nucleic acids from the transgenic yeast cells that differ from the wild type yeast cells.

Preferably the wild type yeast cells are wild type diploid *Saccharomyces cerevisiae* yeast cells, more preferably wild type *Saccharomyces cerevisiae* W303 yeast cells. Furthermore preferably the organism is a plant, which plant preferably is a salt treated plant, more preferably a salt treated halophytic plant or a part thereof, most preferably salt treated *Beta vulgaris* or a part thereof.

The use of yeast cells for identifying genes involved in salt or osmotic stress is known in the art. Yeast is a good model organism for testing genes conferring tolerance to osmotic or salt stress because suitable mutants are known that allow for complementation. WO 02/052012 teaches a screening method wherein a mutant salt sensitive yeast strain is transformed with cDNA isolated from salt stresses sugar beet. The method resulted in the identification of genes that may contribute to increased tolerance to salt, drought or osmotic stress in plants. Here, for the first time yeast was used for screening a plant cDNA library involving the application of cold stress. In contrast to WO 02/052012, where a mutation causing salt sensitivity is to be complemented by an introduced plant cDNA, wild type yeast was used in the present invention instead of a mutant; the wild type yeast was diploid to avoid any effects of recessive chromosomal mutations that would eventually result in cold tolerance of the yeast host. The present invention demonstrates that, since no suitable cold sensitive mutants exist, wild type yeast cells transformed with cDNA from salt stressed plants can be used to isolate genes capable of conferring tolerance against cold stress in plants.

The terms "tolerance" and "resistance" are used interchangeably herein.

The first step of the screening method involves providing a cDNA library of coding sequences from any organism, such as plants animals or fungi. According to a preferred feature of the present invention, the cDNA library is made from a plant, preferably a salt treated plant, further preferably a salt treated halophytic plant or a part thereof, more preferably from a salt treated sugar beet plant or a part thereof, most preferably from leaves of salt treated *Beta vulgaris* plants. Sugar beet (*Beta vulgaris*), a relatively halophytic crop plant, provides a potentially good source of cold tolerance genes. Although the present invention is exemplified by use of a sugar beet cDNA library, it is to be understood that other halophytic plants could equally serve the same purpose. The preparation of cDNA libraries is a routine technique well known in the art. The cDNA library preferably comprises copies of essentially all mRNA of the plant cell. Advantageously, coding sequences alone are sufficient.

The second step of the screening method involves introducing the coding sequences into yeast cells. Methods for transformation of yeast, such as electroporation or treatment with Lithium Acetate, and for expressing genes in yeast, including yeast vectors, such as pYES, are well known in the art (see e.g. *Current Protocols in Molecular Biology*, Unit 13 (Ausubel et al., 1994) and the *Guide to Yeast Genetics and Molecular Biology* (Guthrie and Fink, 1991)). Advantageously, coding sequences may be introduced and expressed in yeast using any of several known methods, with the aim of testing tolerance or resistance to stress conditions. According to a preferred feature of the present invention, a vector based on the λ phage is employed, more preferably λPG15 is used for introducing and expressing coding sequences in yeast. Phage λPG15 comprises the excisable expression plasmid pYPGE15 which may be used directly for both *Escherichia coli* and yeast complementation (Brunelli and Pall, Yeast 9, 1309-1318, 1993). A plasmid cDNA library can be recovered from λPG15 using the cre-lox recombinase system (Brunelli and Pall, Yeast 9, 1309-1318, 1993). Preferably, the yeast cells are *Saccharomyces cerevisiae*, more preferably the diploid wild type strain W303 and its diploid mutant deficient for glycerol phosphate dehydrogenase (gpd1). The yeast strain W303 has the genotype MATa/MATα, ADE2/ade2, CAN1/can1-100, CYH2/cyh2, his3-11,15/his3-11,15, LEU1/leu1-c, LEU2/leu2-3,112, trp1-1:URA3:trp1-3'D/trp1-1, ura3-1/ura3-1, and originates from the parent strains W303-1A and W303-1B (Primig et al., *Nat. Genet.* 26, 415-423, 2000). The W303 gpd1 mutant was unexpectedly more cold tolerant than the W303 wild type strain (see FIG. 1). For this reason the wild type strain was used in the screening, while the gpd1 mutant strain served as a standard for comparison. It was thus expected that nucleic acids conferring cold tolerance would enhance the growth of the wild type yeast cells to a comparable or better level to that of the gpd1 mutant.

Advantageously, the gpd1 gene can be used for enhancing cold tolerance of yeast, for example baker's yeast. Yeast is known to be sensitive to cold stress. Freezing stress in particular has a negative impact on the quality of yeast as a leaven. Yeast cells that have been mutated or engineered such that the glycerol phosphate dehydrogenase (gpd1) gene is inactivated (using techniques known in the art) are surprisingly more tolerant to cold and/or freezing stress than wild type yeast. This trait can be of benefit in, for example, the baking or brewing industries. The present invention thus also provides a method for increasing cold tolerance of yeast cells, comprising downregulating expression in yeast of a nucleic acid encoding a glycerol phosphate dehydrogenase and/or inhibiting activity of a glycerol phosphate dehydrogenase. The invention furthermore provides for the use of a gpd1 gene for altering the stress tolerance of yeast by downregulating its expression. The stress-tolerant yeast cells thus obtained can be used in purified form (for example leaven) or in compositions (for example dough).

The third step of the screen involves growing the yeast cells under stressed conditions. Yeast cells transformed with cDNA of the salt stressed sugar beet were plated onto a suitable medium and grown under cold stress. A temperature of 10° C. was chosen, as this still allowed a minimal growth of the yeast strain, but a person skilled in the art may choose any other temperature below the optimal growth temperature. After a certain period of time colonies that were able to grow under these conditions of cold were selected and their cold tolerance was retested by growing the transgenic cells again under cold stress conditions Advantageously, the cDNA from salt treated plants may also be a suitable basis for finding genes capable for conferring tolerance against other stresses. This may be achieved simply by growing the yeast cells in step (iii) above in conditions of stress determined by the type of gene sought. For example, in order to identify genes conferring tolerance or resistance to heat stress, the yeast cells would be grown in conditions of heat. According to a preferred feature of the invention, the stress is preferably cold stress. It was then determined whether the stress tolerance originated from the transgene and not from a mutation in the host genome. To this end, the plasmid comprising the transgene was cured from a transgenic cold tolerant yeast clone and it was verified whether the cold tolerance had disappeared too; secondly the plasmid comprising the transgene was isolated from a transgenic cold tolerant yeast clone and reintroduced into a non-transgenic yeast strain, whereafter the cold tolerance of the newly transformed yeast strain was compared to the non-transformed yeast strain.

The fourth step in the screening method is the identification of fast growing yeast cells. Yeast cells transformed with a plant nucleic acid conferring stress resistance were identified based on their ability to grow faster under stress conditions than yeast cells not transformed with such a nucleic acid, although other selection criteria may also be used, depending on the type of stress that is applied.

Finally, in the last step of the screening method nucleic acids conferring stress tolerance are isolated from the yeast host and characterised. Methods for isolating nucleic acids from yeast and sequencing these nucleic acids are known to those skilled in the art.

The present invention also encompasses the use of the screening method described above for identifying nucleic acids encoding proteins capable of conferring cold stress tolerance to plant cells or yeast cells.

The screening method described above yielded several nucleic acids encoding proteins that increase cold stress tolerance of the yeast strain, hereafter named CRYO genes and CRYO proteins. The proteins encoded by these nucleic acids all relate to vesicle trafficking to the vacuole or plasma membrane. Response to stress requires an adaptation of metabolism, including transport of proteins and other components between different organelles, in particular between the Golgi apparatus and the vacuole, but also between the plasma membrane and the vacuole. Plant vacuoles perform different functions, depending on the cell type in which they occur. They play an important role in cell growth or function as storage organelles for proteins, ions, secondary metabolites and metabolic waste products. In this last aspect, vacuoles also resemble lysosomes. They contain many hydrolytic enzymes for degradation of damaged or redundant cell material. Adaptation to changing environmental conditions or to stress involves not only synthesis of new cellular components, but also degradation of cellular material. These degradation processes require an extensive trafficking of material via membrane bound vesicles such as endosomes. Also hydrolytic enzymes are delivered to the vacuole via endosomes.

CRYO4 (SEQ ID NO 8) is a protein with homology to At1g72160, a cytosolic factor in *Arabidopsis thaliana*, and it further has significant homology with yeast SEC14 (=YMR079W). This yeast protein is a cytosolic phosphatidylinositol/phosphatidylcholine transfer protein and is required for the transport of secretory proteins from the Golgi complex and for protein secretion (Bankaitis et al., (1990) Nature 347, 561-562). In yeast it is associated with the Golgi complex as a peripheral membrane protein and forms a link between phospholipid metabolism and vesicle trafficking (Li et al., (2000) Mol. Biol. Cell 11, 1989-2005). It catalyses the transfer of phosphatidylinositol and phosphatidylcholine between membranes in vitro and is essential for viability and secretion (Tschopp et al., (1984) J. Bacteriol 160, 966-970). CRYO5 (SEQ ID NO 10) is a protein with a RING-domain. RING-domain proteins are known to be involved in biological processes such as transcriptional and translational regulation, and in targeted proteolysis. The RING-domain mediates protein-protein interactions and is a C3HC4 type zinc-finger domain of 40 to 60 amino acids long. Various proteins with a RING finger domain exhibit binding to E2 ubiquitin-conjugating enzymes (Ubc's) (Freemont (2000) Curr Biol. 10, R84-87). The above domain Zf-RING finger is different from that found in yeast CLASS E vacuolar sorting protein VPS27. However, there may be some functional conservation since VPS27 has also been linked to ubiquitination processes and protein turnover, and the Zf-RING finger domain present in CRIO5 is usually found in proteins that are also involved in ubiquitination and proteasome protein degradation.

The other proteins of the present invention belong to the group of Class-E vacuolar trafficking mutants. Certain mutants in yeast, known as "Class-E" mutants (Jones et al., In: Yeast III, Cold Spring Harbor Laboratory Press, p 363-470, 1997), are unable to perform a correct sorting of proteins to the vacuole. Microscopical analysis reveals that these mutants contain large aberrant endosomal structures (Raymond et al., Molecular Biology of the Cell 3, 1389, 1992), filled with proteins that are normally transited to the vacuole.

CRYO1, CRYO2 and CRYO3 all have a SNF7 domain (Pfam PF03357/IPR005024; Pfam database, Bateman et al., (2004) Nucleic Acids Research Database Issue 32, D138-D141). Structurally, the three proteins belong to the family of CHMP proteins (Howard et al., (2001) J. Cell Sci. 114, 2395-2404). CRYO1 (SEQ ID NO: 2) and CRYO2 (SEQ ID NO: 4) are isoforms of each other. CRYO1 and its plant homologues have not yet been functionally characterised, but they are related to yeast SNF7 (=DID1=VPS32=YLR025W). SNF7 mutants belong to the group of class E vacuolar trafficking mutants (Jones et al., In: Yeast III, Cold Spring Harbor Laboratory Press, p 363-470, 1997). The SNF7 mutant accumulates a prominent organelle distinct from the vacuole, containing large amounts of enzymes which are normally present in the vacuole such as the hydrolases CpY, PrA & PrB. The protein is involved in derepression of SUC2 in response to glucose limitation. SNF7 mutants show a decrease in invertase derepression, a growth defect on raffinose, temperature-sensitive growth on glucose, and a sporulation defect in homozygous diploids. The SNF7 sugar related phenotype could be due to an altered turnover of a glucose sensor. These and other data suggest that the protein transport from the Golgi network and from the plasma membrane to the vacuole is interfered with. SNF7 forms a family of coiled-coil-forming proteins with vps20 and mos10. The proteins are involved in same trafficking step, endosome-to-vacuole transport, but probably participate in different cargo-specific events (Kranz et al., 2001).

SEQ ID NO: 6 (CRYO3) is the plant homologue of yeast DID2 (=FT11=YKR035W-A), another member of the class E vacuolar trafficking proteins. DID2 is related to SNF7; it has similar structural features, it may have a comparable function and possibly belongs to the same protein complex in yeast (Amerik et al., Molecular Biology of the Cell, 11, 3365-3380, 2000). A human orthologue, CHMP1, is reported to be involved in membrane trafficking and localises to early endosomes (Howard et al., 2001). CHMP1 also localises to the nuclear matrix, thereby affecting chromatin structure and cell-cycle progression and furthermore interacts with the PcG protein Polycomblike (Pcl) (Stauffer et al., 2001 J Cell Sci. 114, 2383-93).

Besides modifying tolerance to cold stress, the proteins may also be involved in protein transport and sorting (CRYO1 [SEQ ID NOs: 1/2], CRYO2 [SEQ ID NOs: 3/4], CRYO3 [SEQ ID NOs: 5/6] and CRYO4 [SEQ ID NOs: 7/8]), vacuole formation, development or functioning (CRYO1, CRYO2, CRYO3), in transcription and translation (CRYO3, CRYO5), in membrane fluidity (CRYO4) and in protein turnover (CRYO5).

The proteins encoded by the nucleic acids identified by the screening method according to the present invention were hitherto unknown. Therefore, the invention also provides an isolated CRYO protein, (a) comprising the sequence as given in SEQ ID NOs: 2, 4, 6, 8 or 10;
(b) comprising a sequence having at least
  i. 76%, alternatively 80%, preferably 90%, more preferably 95%, 96%, 97%, 98% or 99% sequence identity to the full length sequence as given in SEQ ID NO: 2;
  ii. 55%, alternatively 60%, 70%, 80%, preferably 90%, more preferably 95%, 96%, 97%, 98% or 99% sequence identity to the full length sequence as given in SEQ ID NO: 4;
  iii. 90.5%, alternatively 90.6%, 90.7%, 90.8%, 90.9%, preferably 91%, 92%, 93%, 94% more preferably 95%, 96%, 97%, 98% or 99% sequence identity to the full length sequence as given in SEQ ID NO: 6;
  iv. 50%, alternatively 60%, 70%, 80%, preferably 90%, more preferably 95%, 96%, 97%, 98% or 99% sequence identity to the full length sequence as given in SEQ ID NO: 8;
  v. 50%, alternatively 60%, 70%, 80%, preferably 90%, more preferably 95%, 96%, 97%, 98% or 99% sequence identity to the full length sequence as given in SEQ ID NO:10;
(c) comprising a substitution variant or insertion variant of (a);
(d) according to any of (a) to (c), comprising substitutions with corresponding naturally or non-naturally altered amino acids;

A CRYO gene according to the present invention is any nucleic acid encoding a CRYO protein as defined above.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company). The homologues useful in the methods according to the invention have in the case of CRYO4 or CRYO5 at least 50% sequence identity or similarity (functional identity) to the unmodified protein, alternatively at least 60% sequence identity or similarity to an unmodified protein, or alternatively at least 70% sequence identity or similarity to an unmodified protein. Typically, the homologues of CRYO4 or CRYO5 have at least 80% sequence identity or similarity to an unmodified protein, preferably at least 85% sequence identity or similarity, further preferably at least 90% sequence identity or similarity to an unmodified protein, most preferably at least 95% sequence identity or similarity to an unmodified protein. In the case of CRYO2, the homologues useful in the methods according to the invention have at least 55% sequence identity or similarity (functional identity) to the unmodified protein, alternatively at least 60% sequence identity or similarity to an unmodified protein, or alternatively at least 70% sequence identity or similarity to an unmodified protein. Typically, the homologues of CRYO2 have at least 80% sequence identity or similarity to an unmodified protein, preferably at least 85% sequence identity or similarity, further preferably at least 90% sequence identity or similarity to an unmodified protein, most preferably at least 95% sequence identity or similarity to an unmodified protein. In the case of CRYO1, the homologues useful in the methods according to the invention have at least 76% sequence identity or similarity (functional identity) to the unmodified protein. Typically, the homologues of CRYO1 have at least 80% sequence identity or similarity to an unmodified protein, preferably at least 85% sequence identity or similarity, further preferably at least 90% sequence identity or similarity to an unmodified protein, most preferably at least 95% sequence identity or similarity to an unmodified protein. In the case of CRYO3, the homologues useful in the methods according to the invention have at least 90.5% sequence identity or similarity (functional identity) to the unmodified protein. Typically, the homologues of CRYO3 have at least 91% sequence identity or similarity to an unmodified protein, preferably at least 92% sequence identity or similarity, further preferably at least 93% sequence identity or similarity to an unmodified protein, most preferably at least 95% sequence identity or similarity to an unmodified protein. Furthermore, homologues of a CRYO protein according to the present invention are capable of increasing the cold stress tolerance of yeast in an assay as outlined above.

Two special forms of homology, orthologous and paralogous, are evolutionary concepts used to describe ancestral relationships of genes. The term "paralogous" relates to gene-duplications within the genome of a species leading to paralogous genes. The term "orthologous" relates to homologous genes in different organisms due to ancestral relationship.

The term "homologues" as used herein also encompasses paralogues and orthologues of the proteins useful in the methods according to the invention.

Orthologues in other plant species may easily be found by performing a so-called reciprocal blast search. This may be done by a first blast involving blasting the sequence in question (any one of SEQ ID NOs: 1 to 10) against any sequence databases, such as the publicly available NCBI database which may be found at: URL ncbi.nlm.nih.gov. If orthologues in rice are sought, the sequence in question would be blasted against, for example, the 28,469 full-length cDNA clones from *Oryza sativa* Nipponbare available at NCBI. BLASTn may be used when starting from nucleotides or TBLASTX when starting from the protein, with standard default values. The blast results may be filtered. The full-length sequences of either the filtered results or the non-filtered results are then blasted back (second blast) against the sequence in question. The results of the first and second blasts are then compared. True orthologues are those that match again with the query gene. In the case of large families, ClustalW and the neighbour joining method is used to construct a phylogenetic tree to help visualize the clustering.

Homologous proteins can be grouped in "protein families". A protein family can be defined by functional and sequence similarity analysis, such as, for example, Clustal W. A neighbour-joining tree of the proteins homologous to a protein of interest can be generated by the Clustal W program and gives a good overview of their structural and ancestral relationships.

The CRYO1, CRYO2 or CRYO3 proteins comprise a SNF7 domain and can be regarded as members of the same protein family as human CHMP1 and yeast SNF7. The SNF7 domain (Pfam PF03357) occurs in a group of proteins involved in protein sorting and transport from the endosome to the vacuole/lysosome in eukaryotic cells. In the Interpro database, the SNF7 family is described as a family of eukaryotic proteins which are variously described as either hypothetical protein, developmental protein or related to yeast SNF7. The family contains human CHMP1. CHMP1 (CHromatin Modifying Protein; CHarged Multivesicular body Protein) is encoded by an alternative open reading frame in the PRSM1 gene and is conserved in both complex and simple eukaryotes. CHMP1 contains a predicted bipartite nuclear localisation signal and distributes as distinct forms to the cytoplasm and the nuclear matrix in all cell lines tested. Human CHMP1 is strongly implicated in multivesicular body formation. A multivesicular body is a vesicle-filled endosome that targets proteins to the interior of lysosomes. Immunocytochemistry and biochemical fractionation localise CHMP1 to early endosomes and CHMP1 physically interacts with SKD1/VPS4, a highly conserved protein directly linked to multivesicular body sorting in yeast. Similar to the action of a mutant SKD1 protein, over expression of a fusion derivative of human CHMP1 dilates endosomal compartments and disrupts the normal distribution of several endosomal markers. Genetic studies in *Saccharomyces cerevisiae* further support a conserved role of CHMP1 in vesicle trafficking. Deletion of CHM1, the budding yeast homolog of CHMP1, results in defective sorting of carboxypeptidases S and Y and produces abnormal, multi-lamellar prevacuolar compartments. This phenotype classifies CHM1 as a member of the class E vacuolar protein sorting genes. In this CHMP family other CHMP proteins can be found, such as the yeast proteins Chm1p, Chm2p, Vps24p, Chm5p and Chm6p, or the human proteins AF281064, AF042384, AF151842, AF19226, AF161483, AF132968 and AW965590 (Howard et al., 2001). All these proteins constitute a family of structurally related proteins with a similar size and charge distribution (basic N-terminus and acidic C-terminus) and sequence conservation throughout the complete protein sequence (Howard et al., 2001). This structural conservation indicates also a functional conservation: CHM gene products are involved in correct sorting of carboxypeptidase Y and can be assayed in a pulse chase experiment as described by Howard et al. (2001).

CRYO4 belongs to the same family as yeast SEC14. CRYO4 comprises a SEC14 domain as defined in the SMART database (Schultz et al. (1998) Proc. Natl. Acad. Sci. USA 95, 5857-5864; Letunic et al. (2004) Nucleic Acids Res 32, D142-D144): the SEC14 domain is found in homologues of a *S. cerevisiae* phosphatidylinositol transfer protein (Sec14p) and in RhoGAPs, RhoGEFs and the RasGAP, neurofibromin (NF1). It is also reported to be a lipid-binding domain. The SEC14 domain of Dbl is known to associate with G protein beta/gamma subunits. This domain is also described in the Interpro database (Mulder et al., (2003) Nucl. Acids. Res. 31, 315-318) (IPR001251), where the proteins comprising this domain are grouped as a family of various retinaldehyde/retinal-binding proteins that may be functional components of the visual cycle in animals. Cellular retinaldehyde-binding protein (CRALBP) carries 11-cis-retinol or 11-cis-retinaldehyde as endogenous ligands and may function as a substrate carrier protein that modulates interaction of these retinoids with visual cycle enzymes. The multidomain protein Trio binds the LAR transmembrane tyrosine phosphatase, contains a protein kinase domain, and has separate rac-specific and rho-specific guanine nucleotide exchange factor domains. Trio is a multifunctional protein that integrates and amplifies signals involved in coordinating actin remodeling, which is necessary for cell migration and growth. Other members of the family are transfer proteins that include, guanine nucleotide exchange factor that may function as an effector of RAC1, phosphatidylinositol/phosphatidylcholine transfer protein that is required for the transport of secretory proteins from the Golgi complex and alpha-tocopherol transfer protein that enhances the transfer of the ligand between separate membranes. Homologues useful in the present invention comprise a SEC14 domain and exhibit lipid transfer activity (a suitable assay is described by Jouannic et al., Eur. J. Biochem. 258, 402-410 (1998)) and include for example the *Arabidopsis* proteins At1g72160, At4g09160, At1g22530, At1g72150, At3g51670, At1g30690, the rice protein BAB86220 and the maize protein encoded by AY107978.

CRYO5 comprises a RING type zinc finger domain in the carboxy-terminal part of the protein, in addition there is a conserved sequence spanning amino acid (AA) 15 to 305 of SEQ ID NO: 10 that corresponds to a Pfam-B__23829 domain (which domain is postulated to be associated with the C3HC4 type Zn-finger domain) and a sequence from AA 425 to 473, corresponding to Pfam-B__2377. The CRYO5 sequence corresponding to this Pfam-B__2377 domain comprises a conserved stretch of amino acids that is also found in other homologous plant proteins and includes of the sequence HDQHRDMRLDIDNMSYEELLALEERIG (SEQ ID NO:11), in which less than 7 mismatches may occur among the various homologues. Plant homologues of CRYO5 constitute a new class of proteins (CRYO5-like proteins) characterised by the presence of a serine rich region in the N-terminal half of the protein, an acidic region that comprises the conserved sequence signature hereabove and the RING finger domain. Exemplary homologues include sequences NP__196626, NP__974832, NP__568462.2, and the protein encoded by AK066069.

Advantageously, homologous proteins belonging to these families and/or comprising one or more of these domains may be useful in the methods of the present invention for conferring abiotic stress tolerance and in particular cold stress tolerance to plant cells or yeast.

Two polypeptides or nucleic acids are said to be "identical" if the sequence of amino acid residues or nucleotides, respectively, in the two sequences is the same when optimally aligned. Sequence comparisons between two (or more) polypeptide or nucleic acids are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150, in which a sequence may be compared to a reference sequence of the same number of contiguous positions after the two sequences are optimally aligned. Optimal alignment of sequences for comparison may be conducted by the local homology algorithm of Smith and Waterman (Adv. Appl. Math. 2, 482, 1981), by the homology alignment algorithm of Needleman and Wunsch (J. Mol. Biol. 48 443, 1970), by the search for similarity method of Pearson and Lipman (Proc. Nat. Acad. Sci. 85, 2444, 1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection. When the Needleman-Wunsch algorithm is used, a gap opening penalty of 10 or 11, a gap extension penalty of 0.5 or 1 is used and where possible, full-length sequences are compared to each other.

The term "derivatives" refers to peptides, oligopeptides, polypeptides, proteins and enzymes which may comprise substitutions, deletions or additions of naturally and non-naturally occurring amino acid residues compared to the amino acid of a naturally-occurring form of the proteins as presented in SEQ ID NOs: 2, 4, 6, 8 or 10. "Derivatives" of a protein comprise proteins in which amino acid residues are substituted by corresponding naturally or non-naturally altered amino acids. "Derivatives" of a protein encompass peptides, oligopeptides, polypeptides, proteins and enzymes which may comprise naturally occurring altered, (such as glycosylated, acylated, myristoylated or phosphorylated amino acids) or non-naturally occurring amino acid residues (such as biotinylated amino acids, or amino acids modified after CNBr treatment) compared to the amino acid of a naturally-occurring form of the polypeptide. "Derivatives" of a protein also encompass proteins carrying post-translational modifications. A derivative may also comprise one or more non-amino acid substituents compared to the amino acid from which it is derived, for example a reporter molecule or other ligand, covalently or non-covalently bound to the amino acid such as, for example, a reporter molecule which is bound to facilitate its detection, and non-naturally occurring amino acid residues relative to the amino acid of a naturally-occurring protein. "Substitutional variants" of a protein are those in which at least one residue in an amino acid has been removed and a different residue inserted in its place. Amino acid substitutions are typically of single residues, but may be clustered depending upon functional constraints placed upon the polypeptide; insertions will usually be of the order of about 1-10 amino acid residues, and deletions will range from about 1-20 residues. Preferably, amino acid substitutions comprise conservative amino acid substitutions. "Insertional variants" of a protein are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid will be smaller than amino- or carboxy-terminal fusions, in the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope. "Functional fragments" or "deletion variants" of a protein are characterised by the removal of one or more amino acids from the protein, such that the remaining fragment still retains the biological activity of the unmodified protein, for example the capacity of conferring cold stress to yeast in an assay detailed in examples 2 and 3. Such "functional fragments" of a protein encompasses at least fifteen contiguous amino acid residues of a protein, in case of a functional fragment the minimum size being a sequence of sufficient size to provide this sequence with at least a comparable function and/or activity to the original sequence which was truncated, while the maximum size is not critical. Typically, the truncated amino acid will range from about 5 to about 60 amino acids in length. "Immunologically active" refers to molecules or specific fragments thereof, such as specific epitopes or haptens, that are recognised by (i.e. that bind to) antibodies. Specific epitopes may be determined using, for example, peptide-scanning techniques as described in Geysen et al., (Chem Biol. 3, 679-688, 1996). Functional fragments can also include those comprising an epitope which is specific for the proteins according to the invention.

Preferably, the derivatives, functional fragments, substitution, deletion or insertion variants of a CRYO protein have at least the same or better functional activity than the unmodified protein, such as the capability of increasing the cold stress tolerance of yeast. The functional activity can be tested with for example the screening method as described above or with methods described for related proteins.

Amino acid variants of a protein may readily be made using peptide synthetic techniques well known in the art, such as solid phase peptide synthesis and the like, or by recombinant DNA manipulations. The manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Another embodiment of the present invention provides nucleic acids obtainable by the screening method according to the present invention, which nucleic acids can be used to modify stress tolerance or resistance in plants and/or yeast. The screening method according to the invention identified several nucleic acids hitherto unknown. The present invention therefore also provides an isolated nucleic acid encoding a protein as defined above, the complement thereof or a part thereof.

The terms "nucleic acid(s)", "nucleotide sequence(s)", "gene(s)", "polynucleotide(s)" and "nucleic acid molecule(s)" are used herein interchangeably to refer to ribonucleotides or deoxyribonucleotides or a combination of both, in a polymeric form of any length. The terms also include double-stranded and single-stranded DNA and RNA. Also included are known nucleotide modifications such as methylation, cyclization and 'caps' and substitution of one or more naturally occurring nucleotides with an analogue such as inosine. The terms also encompass peptide nucleic acids (PNAs).

Advantageously, the nucleic acids according to the invention may be produced using recombinant or synthetic means, such as, for example, PCR cloning mechanisms. Generally, such techniques as defined herein are well known in the art, for example as described in Sambrook et al. (Molecular Cloning: a Laboratory Manual, 2001). Polynucleotides may also be synthesized by well-known techniques as described in the technical literature. See, e.g., Caruthers et al., Cold Spring Harbor Symp. Quant. Biol. 47, 411-418 (1982), and Adams et al., J. Am. Chem. Soc. 105, 661 (1983). Double stranded DNA fragments may then be obtained either by synthesizing the complementary strand and annealing the strands together under appropriate conditions, or by adding the complementary strand using DNA polymerase with an appropriate primer sequence.

A nucleotide sequence encoding a protein (gene, coding sequence, open reading frame or ORF) is a nucleotide sequence that can be transcribed into mRNA and/or translated into a polypeptide when present in an expressible format, i.e. when the coding sequence or ORF is placed under the control of appropriate control sequences or regulatory sequences. A coding sequence or ORF is bounded by a 5' translation start codon and a 3' translation stop codon. A coding sequence or ORF can include, but is not limited to RNA, mRNA, cDNA, recombinant nucleotide sequences, synthetically manufactured nucleotide sequences or genomic DNA. The coding sequence or ORF can be interrupted by intervening nucleic acids.

By "expressible format" is meant that the isolated nucleic acid molecule is in a form suitable for being transcribed into mRNA and/or translated to produce a protein, either constitutively or following induction by an intracellular or extracellular signal, such as an environmental stimulus or stress (mitogens, anoxia, hypoxia, temperature, salt, light, dehydration, etc) or a chemical compound such as IPTG (isopropyl-β-D-thiogalactopyranoside), or such as an antibiotic (tetracycline, ampicillin, rifampicin, kanamycin), hormone (e.g. gibberellin, auxin, cytokinin, glucocorticoid, brassinosteroid, ethylene, abscisic acid etc), hormone analogue (indolacetic acid (IAA), 2,4-D, etc), metal (zinc, copper, iron, etc), or dexamethasone, amongst others. As will be known to those skilled in the art, expression of a functional protein may also require one or more post-translational modifications, such as glycosylation, phosphorylation, dephosphorylation, or one or more protein-protein interactions, amongst others. All such processes are included within the scope of the term "expressible format".

Genes and coding sequences essentially encoding the same protein but isolated from different sources can consist of substantially divergent nucleic acids. Reciprocally, substantially divergent nucleic acids can be designed to effect expression of essentially the same protein. These nucleic acids are the result of e.g. the existence of different alleles of a given gene, or of the degeneracy of the genetic code or of differences in codon usage. Differences in preferred codon usage are illustrated in URL kazusa.or.jp/codon. Allelic variants are further defined as to comprise single nucleotide polymorphisms (SNPs) as well as small insertion/deletion polymorphisms (INDELs, having a size of usually less than 100 bp). SNPs and INDELs form the largest set of sequence variants in naturally occurring polymorphic strains of most organisms. Additionally or alternatively, in particular conventional breeding programs, such as for example marker assisted breeding, it is sometimes practical to introduce allelic variation in the plants by mutagenic treatment of a plant. One suitable mutagenic method is EMS mutagenesis. Identification of allelic variants then takes place by, for example, PCR. This is followed by a selection step for selection of superior allelic variants of the sequence in question and which give rise to altered growth characteristics. Selection is typically carried out by monitoring growth performance of plants containing different allelic variants of the sequence in question (for example SEQ ID NOs: 1, 3, 5, 7 or 9). Monitoring growth performance can be done in a greenhouse or in the field. Further optional steps include crossing plants in which the superior allelic variant was identified with another plant. This could be used, for example, to make a combination of interesting phenotypic features. According to another aspect of the present invention, advantage may be taken of the nucleotide sequence capable of modulating expression of a nucleic acid encoding a CRYO protein (such as SEQ ID NOs: 2, 4, 6, 8 or 10) in breeding programs. For example, in such a program, a DNA marker is identified which may be genetically linked to the gene capable of modulating the activity of a protein of interest (for example SEQ ID NOs: 2, 4, 6, 8 or 10) in a plant (which gene can be the gene encoding a protein of interest or another gene capable of influencing the activity of a protein of interest). This DNA marker is then used in breeding programs to select plants having altered growth characteristics. Many techniques are nowadays available to identify SNPs and/or INDELs.

Also within the scope of the present invention are nucleic acids which are alternative splice variants of a CRYO protein encoded by any one of SEQ ID NOs: 1, 3, 5, 7 or 9. The term "alternative splice variant" as used herein encompasses variants of a nucleic acid encoding a CRYO protein in which selected introns and exons have been excised, replaced or added, optionally in response to specific signals. Methods for the determination of intron and exon positions in a genomic sequence of a gene are known in the art. Splice variants all originate from one and the same pre-mRNA. The splicing occurs after transcription of the gene but before mRNA translation, and is usually regulated in a tissue specific or temporal way (for example, such that the mRNA has tissue-specific expression, see for example Burge et al., (1999). Splicing of precursors to mRNAs by the spliceosomes. In The RNA World II, Gesteland, Cech, and Atkins, eds. (Cold Spring Harbor, N.Y., Cold Spring Harbor Laboratory Press), pp. 525-560). Preferred variants will be ones in which the biological activity of the protein remains unaffected, which can be achieved by selectively retaining functional segments of the protein. Methods for making such splice variants are well known in the art, for example by RNAi (Celotto and Graveley (2002) RNA 8, 718-724), with ribozymes, by introducing mutations in the gene, by modifying the spliceosome or by modifying the signal transduction pathways inducing alternative splicing.

The invention furthermore encompasses nucleic acids that are capable of hybridising with a nucleic acid encoding a protein as represented by SEQ ID NOs: 2, 4, 6, 8 or 10. The term "hybridisation" as used herein is the process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stringency conditions for hybridisation include high temperature and/or low salt concentration (salts include NaCl and Na$_3$-citrate) and/or the inclusion of formamide in the hybridisation buffer and/or lowering the concentration of compounds such as SDS (detergent) in the hybridisation buffer and/or exclusion of compounds such as dextran sulphate or polyethylene glycol (promoting molecular crowding) from the hybridisation buffer. Conventional hybridisation conditions are described in, for example, Sambrook (2001) Molecular Cloning: a laboratory manual (3rd Edition Cold Spring Harbor Laboratory Press, CSH, New York), but the skilled craftsman will appreciate that numerous different hybridisation conditions can be designed in function of the known or the expected homology and/or length of the nucleic acid. Typical conditions for "stringent hybridisation" are for example hybridising at a temperature of 60° C. followed by washes in 2×SSC, 0.1× SDS, and 1×SSC, 0.1×SDS.

Advantageously, the method according to the present invention may also be practised using portions of a DNA or nucleic acid, which portions encode polypeptides that retain CRYO activity, i.e. a similar biological function to those encoding proteins represented in SEQ ID NOs: 2, 4, 6, 8 or 10. Portions of a DNA sequence refer to a piece of DNA derived or prepared from an original (larger) DNA molecule, which DNA portion, when expressed in a plant, gives rise to plants having modified growth characteristics. The portion may comprise many genes, with or without additional control elements, or may contain just spacer sequences etc.

The term "part of a sequence" means a truncated sequence of the original sequence referred to. The truncated nucleic acid sequence can vary widely in length; the minimum size being a sequence of sufficient size to provide a sequence with at least a comparable function and/or activity or the original sequence referred to, while the maximum size is not critical. In some applications, the maximum size usually is not substantially greater than that required to provide the desired activity and/or function(s) of the original sequence. Typically, the truncated nucleotide sequence will range from about 15 to about 180 nucleotides in length. More typically, however, the sequence will be a maximum of about 150 nucleotides in length, preferably a maximum of about 180 nucleotides. It is usually desirable to select sequences of at least about 30, 36 or 45 nucleotides, up to a maximum of about 60 or 75 nucleotides.

DNA sequences as defined in the current invention can also be interrupted by intervening sequences. With "intervening sequences" is meant any nucleic acid which disrupts a coding sequence in the DNA sequence of interest or which disrupts the expressible format of a DNA sequence comprising the DNA sequence of interest. Removal of intervening sequences restores the coding sequence or said expressible format. Examples of intervening sequences include introns and mobilisable DNA sequences such as transposons. With "mobilisable DNA sequence" is meant any DNA sequence that can be mobilized as the result of a recombination event.

The present invention also relates to a recombinant genetic construct comprising a nucleic acid according to the invention. The genetic constructs facilitate the introduction and/or expression and/or maintenance of a nucleotide sequence as defined above into a plant cell, tissue or organ. Preferably, the genetic construct comprises (i) an isolated nucleic acid encoding a plant protein
   (a) comprising the sequence as given in SEQ ID NOs: 2, 4, 6, 8 or 10;
   (b) comprising a sequence having at least 50%, alternatively 60%, 70%, 80%, preferably 90%, more preferably 95%, 96%, 97%, 98% or 99% sequence identity to the full length sequence as given in SEQ ID NOs: 2, 4, 6, 8 or 10;
   (c) comprising a substitution variant or insertion variant of (a);
   (d) according to any of (a) to (c), comprising substitutions with corresponding naturally or non-naturally altered amino acids;
(ii) a regulatory element operably linked to the nucleic acid of (i), which regulatory element is a plant and/or yeast expressible promoter; and optionally
(iii) a transcription termination sequence.

The nucleic acid construct can be an expression vector wherein the nucleic acid is operably linked to one or more regulatory elements allowing expression in prokaryotic and/ or eukaryotic host cells. The vector may be commercially available, suitable for transforming into plants and suitable for expression of the gene of interest in the transformed cells.

Advantageously, any nucleic acid obtainable by the screening method according to the present invention can be used in the construct; preferably a nucleic acid as defined in any of (a) to (d) above is used.

The term "operably linked" as used herein refers to a functional linkage between the regulatory element and the gene of interest, such that the regulatory element is able to initiate transcription of the gene of interest.

As used herein, the term "plant-expressible promoter" refers to a promoter that is capable of driving transcription in a plant cell. This not only includes any promoter of plant origin, such as the natural promoter of the transcribed DNA sequence, but also any promoter of non-plant origin which is capable of directing transcription in a plant cell. The promoter may also be an artificial or synthetic promoter. The term "plant-expressible promoter" includes, but is not restricted to, constitutive, inducible, organ-, tissue- or cell-specific and/or developmentally regulated promoters. The terms "regulatory element", "control sequence", "promoter" are all used herein interchangeably and, taken in a broad context, refer to regulatory nucleic acids capable of effecting expression of the sequences to which they are ligated.

Advantageously, any type of promoter may be used to drive expression of the nucleic acid encoding a CRYO protein in a plant. More specifically, a constitutive promoter can be, but is not restricted to, one of the following: a 35S promoter (Odell et al., Nature 313, 482-493, 1985), a 35S'3 promoter (Hull and Howell, Virology 86, 482-493, 1987), the promoter of the nopaline synthase gene ("PNOS") of the Ti-plasmid (Herrera-Estrella, Nature 303, 209-213, 1983) or the promoter of the octopine synthase gene ("POCS", De Greve et al., J. Mol. Appl. Genet. 1, 499-511, 1982). It is clear that other constitutive promoters can be used to obtain similar effects. A meristem-specific promoter, such as the rnr (ribonucleotide reductase), cdc2a promoter and the cyc07 promoter, could be used to effect expression in all growing parts of the plant, thereby increasing cell proliferation, which in turn would increase yield or biomass. If the desired outcome would be to influence seed characteristics, such as the storage capacity, seed size, seed number, biomass etc., then a seed-specific promoter, such as p2S2, pPROLAMIN, pOLEOSIN could be selected. An aleurone-specific promoter may be selected in order to increase growth at the moment of germination, thereby increasing the transport of sugars to the embryo. An inflorescence-specific promoter, such as pLEAFY, may be utilised if the desired outcome would be to modify the number of flower organs. To produce male-sterile plants one would need an anther specific promoter. To impact on flower architecture for example petal size, one could choose a petal-specific promoter. If the desired outcome would be to modify growth and/or developmental characteristics in particular organs, then the choice of the promoter would depend on the organ to be modified. For example, use of a root-specific promoter would lead to increased growth and/or increased biomass or yield of the root and/or phenotypic alteration of the root. This would be particularly important where it is the root itself that is the desired end product, such crops include sugar beet, turnip, carrot, and potato. A fruit-specific promoter may be used to modify, for example, the strength of the outer skin of the fruit or to increase the size of the fruit. A green tissue-specific promoter may be used to increase leaf size. A cell wall-specific promoter may be used to increase the rigidity of the cell wall, thereby increasing pathogen resistance. An anther-specific promoter may be used to produce male-sterile plants. A vascular-specific promoter may be used to increase transport from leaves to seeds. A nodule-specific promoter may be used to increase the nitrogen fixing capabilities of a plant, thereby increasing the nutrient levels in a plant. A stress-inducible promoter may also be used to drive expression of a nucleic acid to increase membrane integrity during conditions of stress. A stress inducible promoter such as the water stress induced promoter WSI18, the drought stress induced Trg-31 promoter, the ABA related promoter rab21 or any other promoter which is induced under a particular stress condition such as temperature stress (cold, freezing, heat) or osmotic stress, or drought stress or oxidative stress or biotic stress can be used to drive expression of a CRYO gene.

If the desired outcome would be to influence the cold tolerance of a plant under adverse conditions, then a cold-inducible promoter such as, for example, prd29, pws18 or pcor15 could be selected.

Similarly, the term "yeast-expressible promoter" refers to a promoter that is capable of driving transcription in a yeast cell and encompasses natural yeast promoters as well as other promoter sequences capable of driving expression in yeast cells. Suitable promoters for expression in yeast are known in the art, see for example *Current Protocols in Molecular Biology*, Unit 13 (Ausubel et al., 1994) and the *Guide to Yeast Genetics and Molecular Biology* (Guthrie and Fink, 1991).

The recombinant genetic construct according to the present invention may include further regulatory or other sequences from other genes. Encompassed are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included is a transcriptional regulatory sequence of a classical prokaryotic gene, in which case it may include a −35 box sequence and/or −10 box transcriptional regulatory sequences. Regulatory elements also encompass a synthetic fusion molecule or derivative which confers, activates or enhances expression of a nucleic acid molecule in a cell, tissue or organ.

Optionally, one or more terminator sequences may also be used in the construct introduced into a plant. The term "terminator" encompasses a control sequence which is a DNA sequence, at the end of a transcriptional unit, which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention.

Furthermore, the recombinant nucleic acid can be constructed and employed to target the gene product of the nucleic acid of the invention to a specific intracellular compartment within a plant cell or to direct a protein to the extracellular environment. This can generally be obtained by operably joining a DNA sequence encoding a transit or signal peptide to the recombinant nucleic acid.

The genetic constructs of the invention may further include an origin of replication sequence which is required for maintenance and/or replication in a specific cell type, for example a bacterial cell, when the genetic construct is required to be maintained as an episomal genetic element (e.g. plasmid or cosmid molecule) in a cell. Preferred origins of replication include, but are not limited to, the f1-ori and colE1 origins of replication.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a genetic construct of the invention or a derivative thereof. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include the bar gene which provides resistance to the herbicide Basta; the ampicillin resistance gene ($Amp^r$), the tetracycline resistance gene ($Tc^r$), the bacterial kanamycin resistance gene ($Kan^r$), the phosphinothricin resistance gene, the neomycin phosphotransferase gene (nptII), the hygromycin resistance gene, and the chloramphenicol acetyltransferase (CAT) gene. Visual markers, such as the Green Fluorescent Protein (GFP, Haseloff et al., Nature 334, 585-591, 1997), β-glucuronidase (GUS), and luciferase, may also be used as selectable markers.

According to another embodiment, the present invention relates to the use of the nucleic acids encoding a protein of the present invention or the use of such a protein as selectable marker gene in plants or other organisms. More preferably, the present invention also relates to the use of a gene coding for a CRYO protein as defined above as selectable marker gene, selection taking place by treating with a stress condition such as a sub-optimal growth temperature.

The nucleic acids obtainable by the screening method as described herein encode proteins that support faster growth of yeast under stress conditions, relative to wild type yeast, therefore it is likely, since these nucleic acids originate from plants, that modulation of expression of these nucleic acids upon introduction into plants, will also support faster growth of plants under stress conditions when compared to corresponding wild type plants. Therefore the present invention provides a method for increasing abiotic stress tolerance of plants, comprising the steps of introducing a genetic modification in these plants and selecting for modulated expression in these plants of a nucleic acid sequence encoding a protein
  (a) comprising the sequence as given in SEQ ID NOs: 2, 4, 6, 8 or 10;
  (b) comprising a sequence having at least 50%, alternatively 60%, 70%, 80%, preferably 90%, more preferably 95%, 96%, 97%, 98% or 99% sequence identity to the full length sequence as given in SEQ ID NOs: 2, 4, 6, 8 or 10;
  (c) comprising a substitution variant or insertion variant of (a);
  (d) according to any of (a) to (c), comprising substitutions with corresponding naturally or non-naturally altered amino acids;
  (e) comprising a functional fragment of any of (a) to (d).

Preferably this protein increases cold stress tolerance of yeast. Similarly, the present invention provides a method for increasing stress tolerance of yeast, preferably to cold stress, comprising modulating expression in plants of a nucleic acid sequence encoding a CRYO protein and/or modulating activity of a CRYO protein.

Advantageously, proteins homologous to a CRYO protein can also be used in the methods of the present invention. The invention thus provides a method for increasing abiotic stress tolerance of plants, comprising the steps of introducing a genetic modification in these plants and selecting for modulated expression in these plants of a nucleic acid sequence encoding a protein chosen from the group of
  (i) proteins belonging to the family of CHMP proteins
  (ii) proteins comprising a SEC14 domain and exhibiting lipid transfer activity
  (iii) CRYO5 like plant proteins comprising a RING finger domain, a serine rich domain and an acid domain which comprises the signature HDQHRDMRLDIDNMSY-EELLALEERIG (SEQ ID NO:11), in which no more than 6 substitutions may occur.

"Increased stress tolerance" as used herein comprises, for any given stress, increasing tolerance in plants or yeast to that particular stress, whether those plants or yeast already have some degree of tolerance to the particular stress or whether that plant or yeast is being provided with tolerance to that stress anew.

Preferably, the increased tolerance is to at least one of temperature stress, osmotic stress, drought stress, salt stress or oxidative stress, more preferably cold stress.

The terms "tolerance" and "resistance" as used herein encompass protection against stress ranging from a delay to substantially a complete inhibition of alteration in cellular metabolism, reduced cell growth and/or cell death caused by environmental stress conditions. Advantageously, transgenic plants or yeasts obtained by the methods of the present invention are tolerant or resistant to environmental stress conditions.

The term "environmental stress" as used herein encompasses stress factors such as drought stress (water, dehydration), osmotic stress, salt stress, temperature stress (due to for example heat or frost). "Temperature stress" which includes "cold stress", "chilling stress", "freezing stress" or "heat stress" is a stress induced by sub-optimal or supra-optimal growth temperatures for a particular organism. Optimal growth temperature ranges may be readily determined or would be known to those skilled in the art. "Osmotic stress" is any stress associated with or induced by loss of water, reduced turgor or reduced water content of a cell, tissue, organ or whole plant. "Drought stress" refers to any stress which is induced by or associated with the deprivation of water or reduced supply of water to a cell, tissue, organ or organism. The term "salt-stress" refers to any stress which is associated with or induced by elevated concentrations of salt or ions in general and which result in a perturbation in the osmotic potential of the intracellular or extracellular environment of a cell. "Oxidative stress" occurs in situations of cold stress combined with intensive light, in situations of ozone stress, in cases of necrosis as a result of pathogen infection or wounding, in cases of senescence and due to application of certain herbicides (like atrazine or paraquat).

According to a preferred feature of the invention, the stress is cold stress. Advantageously the results of testing for tolerance or resistance to environmental conditions in the yeast cells give a reliable measure of the capability of the inserted coding sequence or gene to induce tolerance or resistance to environmental stress in plants. The capacity of an isolated nucleic acid to confer tolerance or resistance to environmental stress tolerance to plants can be tested according to methods well-known in the art, see for example, Physical Stresses in Plants: Genes and Their Products for Tolerance. S. Grillo (Editor), A. Leone (Editor) (June 1996), Springer Verlag; ISBN: 3540613471; Handbook of Plant and Crop Stress. Mohammad Peassarakli (Editor), Marcel Dekker, ISBN: 0824789873; The Physiology of Plants Under Stress; Abiotic Factors. Erik T. Nilsen, David M. Orcutt (Contributor), Eric T. Nilsen. $2^{nd}$ edition (October 1996), John Wiley & Sons; ISBN: 047131526; Drought, Salt, Cold and Heat Stress: Molecular Responses in Higher Plants (Biotechnology Intelligence Unit). Kazuo Shinozaki (Editor), Kazuko Yamaguchi-Shinozaki (Editor) (1999). R G Landes Co; ISBN: 1570595631; Plants Under Stress: Biochemistry, Physiology and Ecology and Their Application to Plant Improvement (Society for Experimental Biology Seminar Serie). Hamlyn G. Jones, T. J. Flowers, M. B. Jones (Editor). (September 1989). Cambridge Univ. Pr. (Short); ISBN: 0521344239; Plant Adaptation to Environmental Stress. Leslie Fowden, Terry Mansfield, John Stoddart (Editor) (October 1993) Chapman & Hall; ISBN: 0412490005; or the appended examples. Similar methods exist for yeast; see for example: The molecular and cellular biology of the yeast *Saccharomyces cerevisiae*. Pringle, Jones, Broach and Strathern, Cols Spring Harbor laboratory press, 1992 (New York); Guide to yeast Genetics and Mollecular and Cell Biology (Volum 350 and 351 of Methods in enzymology) (Guthrie and Finf Eds), Academic Press (2002) San Diego; Yeast Gene Analysis (Brown and Tuite) (Volume 26 of Methods in Microbiology) Academic press (San Diego); Yeast Stress Responses (Ed. Hohmann and Mager) Springer Verlag, Heidelberg 1997.

The methods of the present invention encompass a genetic modification of a plant or a plant cell. The term "genetic modification" refers to a change by human intervention in the genetic content of a cell compared to a wild type cell and includes techniques like genetic engineering, breeding or mutagenesis. The change in genetic content comprises modifications of the genome and includes addition, deletion and substitution of genetic material in the chromosomes of a plant cell as well as in episomes. The term also encompasses the addition of extrachromosomal information to a plant cell. Preferably, the genetic modification results in modulated expression of a nucleic acid. The methods of the present invention also encompass a subsequent step of selection, during which plants with the desired characteristics are selected. The selection step may be based on monitoring the presence or absence of modified growth characteristics, or on monitoring the presence or absence of selectable or screenable marker genes linked an introduced nucleic acid of interest.

Modulation (enhancing or decreasing) of expression of a nucleic acid encoding a CRYO protein or modulation of a CRYO protein itself encompasses altered expression of a gene or altered levels of a gene product, namely a polypeptide, in specific cells or tissues, which gene or gene-product influences CRYO gene expression or protein activity.

The nucleic acids obtained by the screening method according to the invention will have the capacity to modify tolerance to cold stress in plants or yeast. This effect may also be obtained by applying the proteins encoded by the nucleic acids as defined above, directly to the plants or yeast.

Preferably, modulation of expression of a nucleic acid encoding a CRYO protein and/or modulation of activity of the CRYO protein itself is effected by recombinant means. Such recombinant means may comprise a direct and/or indirect approach for modulation of expression of a nucleic acid and/or for modulation of the activity of a protein.

For example, an indirect approach may comprise introducing, into a plant, a nucleic acid capable of modulating activity of the protein in question (a CRYO protein) and/or expression of the gene in question (a gene encoding a CRYO protein). The CRYO gene or the CRYO protein may be wild type, i.e. the native or endogenous nucleic acid or polypeptide. Alternatively, it may be a nucleic acid derived from the same or another species, which gene is introduced as a transgene, for example by transformation. This transgene may be substantially modified from its native form in composition and/or genomic environment through deliberate human manipulation. Also encompassed by an indirect approach for modulating activity of a CRYO protein and/or expression of a CRYO gene is the inhibition or stimulation of regulatory sequences that drive expression of the native gene or transgene. Such regulatory sequences may be introduced into a plant.

A direct and more preferred approach comprises introducing into a plant or yeast a nucleic acid encoding a protein, or a functional fragment thereof, as defined above. The nucleic acid may be introduced by, for example, transformation. The nucleic acid may be derived (either directly or indirectly (if subsequently modified)) from any source provided that the sequence, when expressed in a plant or yeast, leads to modulated expression of a CRYO nucleic acid/gene or modulated activity of a CRYO protein.

Preferably, the nucleic acid is isolated from a halophytic plant, more preferably from *Beta vulgaris*. Most preferably, the nucleic acid capable of modulating expression of a CRYO gene or activity of a CRYO protein in a plant is a nucleic acid as represented by SEQ ID NOs: 1, 3, 5, 7, 9, or homologues, derivatives or functional fragments thereof, or a nucleic acid encoding a protein represented by SEQ ID NOs: 2, 4, 6, 8 or 10, or homologues, derivatives or functional fragments thereof.

However, it should be clear that the applicability of the invention is not limited to use of a nucleic acid represented by SEQ ID NOs: 1, 3, 5, 7, 9 nor to the nucleic acid encoding the protein of SEQ ID NOs: 2, 4, 6, 8 or 10, but that other nucleic acids encoding homologues, derivatives or functional fragments of SEQ ID NOs: 1 to 10 may be useful in the methods of the present invention. Advantageously, the method according to the present invention serves to confer tolerance or resistance to environmental stress conditions in plants and parts thereof, or in yeast.

Modulating the activity of a nucleic acid/gene can be achieved for example by inhibiting or stimulating control elements that drive expression of a native gene or of a transgene, such regulatory sequences may be introduced into a plant or yeast. The "nucleic acid" or "protein" may be wild type, i.e. the native or endogenous nucleic acid or polypeptide. Alternatively, the gene may be a heterologous nucleic acid derived from the same or another species, which gene is introduced as a transgene, for example, by transformation. This transgene may be substantially modified from its native form in composition and/or genomic environment through deliberate human manipulation. Modulating gene expression also encompasses altered transcript level of a gene, which can be sufficient to induce certain phenotypic effects.

According to a preferred feature of the present invention, enhanced or increased expression of a nucleic acid is envisaged. Methods for obtaining enhanced or increased expression of genes or gene products are well documented in the art and include, for example, overexpression driven by a strong promoter, the use of transcription enhancers or translation enhancers.

However downregulation of the expression of a nucleic acid may also give rise to modified stress tolerance in a plant or yeast. Advantageously, plants having modified stress tolerance may be obtained by expressing a nucleic acid encoding a CRYO protein in either sense or antisense orientation. Techniques for downregulation are well known in the art. Similar and other approaches for downregulation expression in yeast are known in the art (for example interruption of the ORF with a gene complementing a metabolic defect of the host strain or with a gene from bacteria conferring tolerance to the antibiotics Kanamycin or Geneticin).

Another embodiment of the invention provides host cells comprising a nucleic acid molecule encoding a CRYO protein. Preferred host cells are plant cells or yeast. The polypeptides of the present invention may also be produced by recombinant expression in prokaryotic and eukaryotic engineered cells other than plant cells, such as bacteria, fungi, or animal cells. Suitable expression systems are known to those skilled in the art.

The invention extends to plants or yeast tolerant to abiotic stress, preferably cold stress, which plants or yeast have elevated levels of a protein as defined above compared to corresponding wild type plants or yeast. The present invention thus also encompasses plants obtainable by the methods according to the present invention. The present invention therefore provides plants obtainable by the method according to the present invention, which plants have increased stress tolerance and which plants have altered CRYO protein activity and/or altered expression of a nucleic acid encoding a CRYO protein. In particular, the present invention provides plants with increased tolerance to abiotic stress, preferably cold stress, which plants have increased expression of a nucleic acid encoding a protein, or a functional fragment thereof, chosen from the group of (i) proteins belonging to the family of CHMP proteins;
(ii) proteins comprising a SEC14 domain and exhibiting lipid transfer activity;
(iii) CRYO5 like plant proteins comprising a RING finger domain, a serine rich domain and an acid domain which comprises the signature HDQHRDMRLDIDNMSYEEL-LALEERIG (SEQ ID NO:11), in which no more than 6 substitutions may occur;

which increased tolerance is relative to corresponding wild type plants.

Furthermore, the present invention provides plants with increased tolerance to abiotic stress, preferably cold stress, which plants have increased expression of a nucleic acid encoding a protein (a) comprising the sequence as given in SEQ ID NOs: 2, 4, 6, 8 or 10;
(b) comprising a sequence having at least 50%, alternatively 60%, 70%, 80%, preferably 90%, more preferably 95%, 96%, 97%, 98% or 99% sequence identity to the full length sequence as given in SEQ ID NOs: 2, 4, 6, 8 or 10;
(c) comprising a substitution variant or insertion variant of (a);
(d) according to any of (a) to (c), comprising substitutions with corresponding naturally or non-naturally altered amino acids;
(e) comprising a functional fragment of any of (a) to (d);

when compared to corresponding wild type plants.

The present invention also relates to a method for the production of transgenic plants, plant cells or plant tissues, comprising introduction of a nucleic acid molecule of the invention in an expressible format or a genetic construct as defined above into a plant, plant cell or plant tissue. Therefore, according to a further embodiment of the present invention there is provided a method for producing transgenic plants having modified tolerance to stress, relative to corresponding wild type plants, which method comprises:

(i) introducing into a plant cell a nucleic acid encoding a CRYO protein or a family member of a CRYO protein or a functional fragment thereof; and (ii) regenerating and/or growing a mature plant from said plant cell.

Preferably, the stress is at least one of cold stress, salt stress, osmotic stress, drought stress or oxidative stress. More preferably, the stress is cold stress.

The present invention extends to any plant cell, plant or plant part or yeast cell obtained by any of the methods described herein, and to all plant parts, including harvestable parts of a plant, seeds and propagules thereof. The present invention also encompasses a plant or a part thereof comprising a plant cell transformed with a nucleic acid according to the invention. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention.

The term "plant" as used herein encompasses whole plants, ancestors and progeny of the plants, plant parts, plant cells, tissues and organs. The term "plant" also therefore encompasses suspension cultures, embryos, meristematic regions, callus tissue, leaves, flowers, fruits, seeds, rhizomes, bulbs, roots (including tubers), shoots (including stem cultures), gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising Acanthaceae, Aceraceae, Acoraceae, Adiantaceae, Agavaceae, Aizoaceae, Alismataceae, Alliaceae, Aloeaceae, Alstroemeriaceae, Amaranthaceae, Amaryllidaceae, Anacardiaceae, Anemiaceae, Angiopteridaceae, Annonaceae, Apocynaceae, Aponogetonaceae, Aquifoliaceae, Araceae, Araliaceae, Araucariaceae, Arecaceae, Aristolochiaceae, Asparagaceae, Aspleniaceae, Asteliaceae, Asteraceae, Balsaminaceae, Basellaceae, Bataceae, Begoniaceae, Berberidaceae, Betulaceae, Bignoniaceae, Bixaceae, Blechnaceae, Bombacaceae, Boraginaceae, Brassicaceae: *Alliaria petiolata, Arabidopsis thaliana, Arabis petiolaris, Arabis pumila, Arabis* sp., *Berteroa incana, Biscutella laevigata, Brassica junceae, Brassica napus, Brassica napus* var. *napus, Brassica nigra, Brassica oleracea, Brassica oleracea* var. *gongylo, Capsella bursa-pastoris, Cardamine pratensis, Cochlearia officinalis, Dentaria laciniata, Descurainia pinnata, Draba asprella, Draba verna, Draba, Erysimum asperum, Erysimum asperum, Erysimum capitatum, Lepidiumflavum, Lepidium virginicum, Lesquerella argyraea, Lesquerella densiflora, Lesquerella rubicundula, Lesquerella* sp., *Lobularia maritima, Lunaria annua, Lunaria rediviva, Neobeckia aquatica, Nerisyrenia camporum, Physaria chambersii, Raphanus sativus, Sinapis alba, Stanleya pinnata, Streptanthus cordatus, Thlaspi arvense, Thlaspi rotundifolium*, Bromeliaceae, Buddlejaceae, Burseraceae, Buxaceae, Cabombaceae, Cactaceae, Caesalpiniaceae, Callitrichaceae, Calochortaceae, Calyceraceae, Campanulaceae, Cannabaceae, Cannaceae, Capparaceae, Caprifoliaceae, Caricaceae, Caryophyllaceae, Casuarinaceae, Celastraceae, Chenopodiaceae, Cistaceae, Clusiaceae, Cneoraceae, Cochlospermaceae, Combretaceae, Commelinaceae, Convallariaceae, Convolvulaceae, Comaceae, Corylaceae, Crassulaceae, Crossosomataceae, Cucurbitaceae, Cunoniaceae, Cupressaceae, Cuscutaceae, Cyatheaceae, Cycadaceae, Cyperaceae, Cyrillaceae, Dennstaedtiaceae, Dicksoniaceae, Didiereaceae, Dilleniaceae, Dioscoreaceae, Dipsacaceae, Dipterocarpaceae, Droseraceae, Dryopteridaceae, Ebenaceae, Ehretiaceae, Elaeagnaceae, Elaeocarpaceae, Elatinaceae, Empetraceae, Epacridaceae, Ephedraceae, Equisetaceae, Ericaceae, Eriocaulaceae, Erythroxylaceae, Escalloniaceae, Euphorbiaceae, Eupomatiaceae, Fabaceae, Fagaceae, Flacourtiaceae, Fouquieriaceae, Frankeniaceae, Fumariaceae, Gentianaceae, Geraniaceae, Gesneriaceae, Ginkgoaceae, Globulariaceae, Goodeniaceae, Grossulariaceae, Gunneraceae, Haemodoraceae, Haloragaceae, Hamamelidaceae, Heliconiaceae, Hippocastanaceae, Hyacinthaceae, Hydrangeaceae, Hydrophyllaceae, Hypericaceae, Iridaceae, Isoetaceae, Juglandaceae, Juncaceae, Koeberliniaceae, Krameriaceae, Lamiaceae, Lauraceae, Lecythidaceae, Lemnaceae, Lentibulariaceae, Liliaceae, Limnanthaceae, Limnocharitaceae, Linaceae, Loasaceae, Lobeliaceae, Loganiaceae, Lomandraceae, Lomariopsidaceae, Loranthaceae, Lycopodiaceae, Lythraceae, Magnoliaceae, Malpighiaceae, Malvaceae, Marantaceae, Marcgraviaceae, Marsileaceae, Martyniaceae, Mayacaceae, Melanthiaceae, Melastomataceae, Meliaceae, Melianthaceae, Menispermaceae, Menyanthaceae, Mimosaceae, Monimiaceae, Monotropaceae, Moraceae, Musaceae, Myoporaceae, Myricaceae, Myristicaceae, Myrsinaceae, Myrtaceae, Nelumbonaceae, Nyctaginaceae, Nymphaeaceae, Nyssaceae, Ochnaceae, Oenotheraceae, Oleaceae, Oliniaceae, Onagraceae, Ophioglossaceae, Orchidaceae, Orobanchaceae, Osmundaceae, Oxalidaceae, Paeoniaceae, Pandanaceae, Papaveraceae, Passifloraceae, Pedaliaceae, Philydraceae, Phormiaceae, Phytolaccaceae, Pinaceae, Piperaceae, Pittosporaceae, plantaginaceae, Platanaceae, Plumbaginaceae, Poaceae, Podocarpaceae, Podophyllaceae, Polemoniaceae, Polygalaceae, Polygonaceae, Polypodiaceae, Pontederiaceae, Portulacaceae, Primulaceae, Proteaceae, Pteridaceae, Punicaceae, Pyrolaceae, Rafflesiaceae, Ranunculaceae, Resedaceae, Restionaceae, Rhamnaceae, Rosaceae, Rubiaceae, Ruscaceae, Rutaceae, Salicaceae, Salviniaceae, Santalaceae, Sapindaceae, Sapotaceae, Sarraceniaceae, Saururaceae, Saxifragaceae, Scrophulariaceae, Selaginellaceae, Simaroubaceae, Smilacaceae, Solanaceae, Sparganiaceae, Sterculiaceae, Strelitziaceae, Styracaceae, Taccaceae, Tamaricaceae, Taxaceae, Taxodiaceae, Theaceae, Thelypteridaceae, Thymelaeaceae, Tiliaceae, Trapaceae, Tremandraceae, Trilliaceae, Trochodendraceae, Tropaeolaceae, Tumeraceae, Typhaceae, Ulmaceae, Urticaceae, Valerianaceae, Verbenaceae, Veronicaceae, Violaceae, Viscaceae, Vitaceae, Welwitschiaceae, Winteraceae, Xanthorrhoeaceae, Xerophyllaceae, Xyridaceae, Zamiaceae, Zingiberaceae, and Zygophyllaceae. According to a preferred feature of the present invention, the plant is a monocotyledonous or dicotyledonous plant, such as a crop plant selected from rice, maize, wheat, barley, soybean, sunflower, canola, alfalfa, millet, barley, rapeseed and cotton. Additional species such as amaranth, artichoke, asparagus, broccoli, Brussels sprouts, cabbage, carrot, cauliflower, celery, collard greens, flax, kale, lentil, oilseed rape, okra, onion, potato, sugar beet, sugar cane, tomato, squash, and tea, trees and algae are not excluded. Further advantageously, plants obtained by the methods according to the invention enable crops to be grown with improved yield, growth, development and productivity under stress conditions, preferably under conditions of cold stress. The present invention also enables crops to be grown in areas which would otherwise not be possible.

The gene of interest is preferably introduced into a plant by transformation. The term "transformation" as referred to herein encompasses the transfer of an exogenous polynucleotide into a host cell, irrespective of the method used for transfer. The polynucleotide may be transiently or stably introduced into a host cell and may be maintained non-integrated, for example, as a plasmid, or alternatively, may be integrated into the host genome. The resulting transformed plant cell can then be used to regenerate a transformed plant in a manner known to persons skilled in the art. Transformation of a plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens et al., Nature 296, 72-74, 1982; Negrutiu I. et al., Plant Mol. Biol. 8, 363-373, 1987); electroporation of protoplasts (Shillito et al., Bio/Technol. 3, 1099-1102, 1985); microinjection into plant material (Crossway et al., Mol. Gen. Genet. 202, 179-185, 1986); DNA or RNA-coated particle bombardment (Klein et al., Nature 327, 70 1987) infection with (non-integrative) viruses and the like, *Agrobacterium*-mediated transformation (Cheng et al. 1997—WO 97/48814; Hansen 1998—WO 98/54961, Hiei et al. 1994—WO 94/00977; Hiei et al. 1998—WO 98/17813; Rikiishi et al. 1999—WO 99/04618; Saito et al. 1995—WO 95/06722), including the 'flower dip' transformation method (Bechtold and Pelletier, Methods Mol. Biol. 82, 259-266, 1998; Trieu et al., Plant J. 22, 531-541, 2000).

Generally after transformation, plant cells or cell groupings are selected for the presence of one or more markers which are encoded by plant-expressible genes co-transferred with the gene of interest, following which the transformed material is regenerated into a whole plant. A whole organism may be regenerated from a single transformed or transfected cell, using methods known in the art. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be undertaken using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The invention also provides a method for producing a transgenic yeast cell having modified tolerance to abiotic stress relative to corresponding wild type yeast cells, which method comprises introducing into a yeast cell a nucleic acid encoding a CRYO protein as defined above. In particular, the present invention provides a method for producing transgenic yeast with increased tolerance to abiotic stress, preferably cold stress, relative to corresponding wild type yeast, which method comprises introducing into a yeast cell a nucleic acid encoding a protein, or a functional fragment thereof, chosen from the group of (i) proteins belonging to the family of CHMP proteins;
(ii) proteins comprising a SEC14 domain and exhibiting lipid transfer activity;
(iii) CRYO5 like plant proteins comprising a RING finger domain, a serine rich domain and an acid domain which comprises the signature "HDQHRDMRLDIDNMSYEELLALEERIG", (SEQ ID NO:11) in which no more than 6 substitutions may occur.

Furthermore, the present invention provides a method for producing transgenic yeast with increased tolerance to abiotic stress, preferably cold stress, relative to corresponding wild type yeast, which method comprises introducing into a yeast cell a nucleic acid encoding a protein, or a functional fragment thereof (a) comprising the sequence as given in SEQ ID NOs: 2, 4, 6, 8 or 10;
(b) comprising a sequence having at least 50%, alternatively 60%, 70%, 80%, preferably 90%, more preferably 95%, 96%, 97%, 98% or 99% sequence identity to the full length sequence as given in SEQ ID NOs: 2, 4, 6, 8 or 10;
(c) comprising a substitution variant or insertion variant of (a);
(d) according to any of (a) to (c), comprising substitutions with corresponding naturally or non-naturally altered amino acids;
(e) comprising a functional fragment of any of (a) to (d).

The invention furthermore provides a transgenic yeast cell obtained by the methods of the invention. Preferably, the transgenic yeast cell with increased expression of a nucleic acid encoding a protein as defined here above, or a functional fragment thereof, is tolerant to abiotic stress, preferably cold stress when compared to corresponding wild type yeast cells.

Furthermore, the invention also relates to the use of a nucleic acid encoding a CRYO protein as defined above or of a CRYO protein itself, to modify stress tolerance of plants or parts thereof or of plant cells. The sequences as depicted in SEQ ID NO: 1 to SEQ ID NO: 10 are revealed to be involved in important processes leading to stress tolerance, as exemplified by plants having altered stress tolerance, which plants have been transformed with a nucleic acid sequence encoding a CRYO protein as defined above. Similarly, the invention also relates to the use of a nucleic acid encoding a CRYO protein or of a CRYO protein itself, to modify stress tolerance of yeast. Preferably, the stress is at least one of temperature stress, osmotic stress, drought stress salt stress or oxidative stress.

The present invention encompasses also the use of homologues of a CRYO protein. Therefore the invention relates to the use of a protein or an active fragment thereof, or of a nucleic acid encoding that protein or active fragment thereof, which protein is chosen from
(i) proteins belonging to the family of CHMP proteins;
(ii) proteins comprising a SEC14 domain and exhibiting lipid transfer activity;
(iii) CRYO5 like plant proteins comprising a RING finger domain, a serine rich domain and an acid domain which comprises the signature HDQHRDMRLDIDNMSY-EELLALEERIG (SEQ ID NO:11), in which no more than 6 substitutions may occur.

to modify stress tolerance of plants or parts thereof or of plant cells. Preferably, the stress is at least one of temperature stress, osmotic stress, drought stress salt stress or oxidative stress.

The present invention encompasses also the use of homologues of a CRYO protein. Therefore the invention relates to the use of a protein or of a nucleic acid encoding that protein, which protein
(a) comprises the sequence as given in SEQ ID NOs: 2, 4, 6, 8 or 10;
(b) comprises a sequence having at least 50%, alternatively 60%, 70%, 80%, preferably 90%, more preferably 95%, 96%, 97%, 98% or 99% sequence identity to the full length sequence as given in SEQ ID NOs: 2, 4, 6, 8 or 10;
(c) comprises a substitution variant or insertion variant of (a);
(d) according to any of (a) to (c), comprises substitutions with corresponding naturally or non-naturally altered amino acids;
(e) comprises a functional fragment of any of (a) to (d);

Furthermore, the characteristic of the transgenic plants of the present invention to display tolerance to cold stress conditions can be combined with other approaches to confer cold stress tolerance to plants, e.g., use of osmotic protectants such as mannitol, proline; glycine-betaine, water-channeling proteins, etc. Thus, the approach of the present invention to confer tolerance to environmental stress conditions to plants can be combined with known approaches which include introduction of various stress tolerance genes. Combination of these approaches may have additive and/or synergistic effects in enhancing tolerance or resistance to environmental stress.

The methods of the present invention to create plants with enhanced tolerance to stress can also be combined with other traits of interest, for example:
(i) herbicide tolerance (DE-A 3701623; Stalker, Science 242 (1988), 419),
(ii) insect resistance (Vaek, Plant Cell 5 (1987), 159-169),
(iii) virus resistance (Powell, Science 232 (1986), 738-743; Pappu, World Journal of Microbiology & Biotechnology 11 (1995), 426-437; Lawson, Phytopathology 86 (1996) 56 suppl.),
(iv) ozone resistance (Van Camp, Biotechnol. 12 (1994), 165-168),
(v) improving the preserving of fruits (Oeller, Science 254 (1991), 437-439),
(vi) improvement of starch composition and/or production (Stark, Science 242 (1992), 419; Visser, Mol. Gen. Genet. 225 (1991), 289-296),
(vii) altering lipid composition (Voelker, Science 257 (1992), 72-74),
(viii) production of (bio)polymers (Poirer, Science 256 (1992), 520-523),
(ix) alteration of the flower colour, e.g., by manipulating the anthocyanin and flavonoid biosynthetic pathway (Meyer, Nature 330 (1987), 667-678, WO90/12084),
(x) resistance to bacteria, insects and fungi (Duering, Molecular Breeding 2 (1996), 297-305; Strittmatter, Bio/Technology 13 (1995), 1085-1089; Estruch, Nature Biotechnology 15 (1997), 137-141),
(xi) alteration of alkaloid and/or cardia glycoside composition,
(xii) inducing maintaining male and/or female sterility (EP-A1 0 412 006; EP-A1 0 223 399; WO93/25695);
(xiii) higher longevity of the inflorescences/flowers, and
(xiv) abiotic stress resistance, other than temperature stress

DESCRIPTION OF THE FIGURES

The present invention will now be illustrated with reference to the following figures:

FIG. 1: Cold sensitivity of the wild type (wt) yeast strain compared to the gpd1 mutant. The yeast cells were grown on YPD (top row) or on SD medium (bottom row) at 30° C. (control, left column), at 10° C. (middle column) or at 15° C. (top right). The WT strain showed reduced growth compared to the gpd1 strain.

FIG. 2: Cold tolerance of the wild type yeast strain transformed with the CRYO1, CRYO2, CRYO3, CRYO4 or CRYO5 gene, compared to the wt yeast strain transformed with an empty vector (pYPGE@). (a) Enhanced growth after 10 days at 10° C. of the yeast cells transformed with the CRYO1, CRYO2 or CRYO3 genes, or after 14 days for yeast cells transformed with the CRYO4 gene. (b) Enhanced growth of the yeast cells transformed with the CRYO5 gene compared to wild type yeast transformed with an empty vector (pYPGE). The two left panels are controls grown at 30° C. on YPD medium or SD medium. The two right panels show growth of the same yeast strains grown at 10° C. on YPD medium or SD medium.

FIG. 3: Alignment between sequences of CRYO1 and CRYO2 from sugar beet and their homologues in *Arabidopsis* and yeast. At=*Arabidopsis thaliana*, Bv=*Beta vulgaris* and Sc=*Saccharomyces cerevisiae*.

FIG. 4: Alignment between the sequences of CRYO3 and homologous proteins from various organisms, showing a high degree of conservation among the different species. At=*Arabidopsis thaliana*; Bv=*Beta vulgaris*; Mm=*Mus musculus*; Hs=*Homo sapiens*; Sp=*Schizosaccharomyces pombe*.

EXAMPLES

Figure 5:
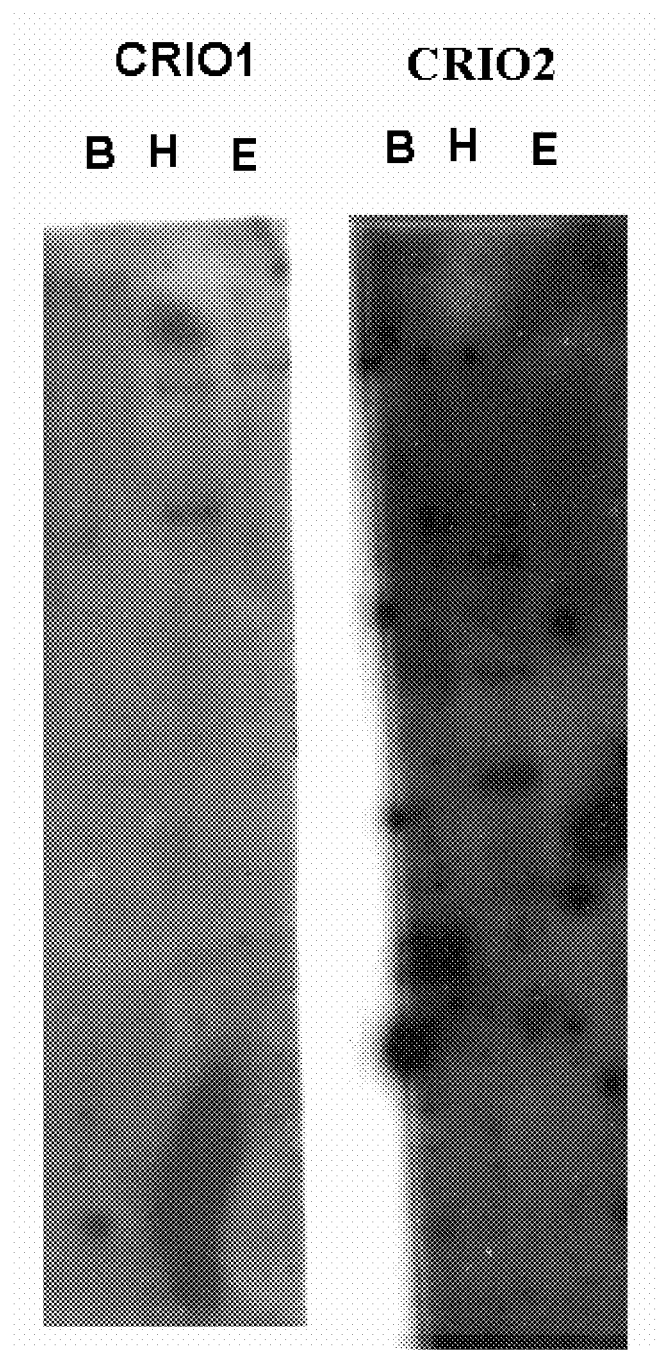
FIG. 5: Southern blot with a CRYO1 and CRYO2 probe on genomic sugar beet DNA. Enzymes used were BamHI, HindIII and EcoRI.

Unless stated otherwise in the Examples, all recombinant DNA techniques are carried out according to standard protocols as described in Sambrook et al. (2001) Molecular Cloning: A Laboratory Manual, Third Edition, Cold Spring Harbor Laboratory Press, NY and in volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd. (UK) and Blackwell Scientific Publications, UK.

Example 1

Construction of a Sugar Beet cDNA Library Induced by Salt Stress

Sugar beet seeds (*Beta vulgaris* cv. Dita) were sown in pots containing a mixture of sand and vermiculite (1:1 w/w). The plants were grown under greenhouse conditions (8 h at 20° C., 16 h at 25° C. with supplementary lighting to ensure a minimum of 12 h photoperiod). The plants were periodically irrigated with a nutrient solution (2.4 g/l Ca(NO3)$_2$.4H$_2$O, 1 g/l KNO$_3$, 1 g/l MgSO$_4$.7H$_2$O, 0.3 g/l KH$_2$PO$_4$, 5.6 mg/l Fequelate (Kelantren, Bayer), 1.1 mg/l ZnSO$_4$.7H$_2$O, 3.3 mg/l MnSO$_4$H$_2$O, 0.3 mg/l CuSO$_4$.5H$_2$O, 3.8 mg/l H$_3$BO$_3$, 0.18 mg/l (NH$_4$)$_6$Mo$_7$.4H$_2$O). For the construction of the cDNA library, 3-week old plants were irrigated with 200 mM NaCl for 24 h before harvesting.

Directional cDNAs were synthesized (cDNA synthesis kit, Stratagene) with poly(A)+ RNA prepared from leaves of salt-treated sugar beet plants. cDNAs were ligated into phage λPG15 vector and packaged with Gigapack III gold packaging extract (Stratagene). A plasmid cDNA library was recovered from λPG15 by the cre-lox recombinase system (Brunelli and Pall, 1993).

Example 2

Setup of a Screening Assay

The yeast strains used in this work were the wild type diploid strain W303/W303 (can1-100, h is 3-11,15,leu2-3, 112, trp1-1,ura3-1,GAL+) (WT) and a mutant deficient for glycerol phosphate dehydrogenase (gpd1). A diploid strain from two gpd1 mutant strains (YRA111 (W303-1A mat a gpd1::TRP1) and YRA114 (W303-1A gpd1::TRP1 mat α)) was constructed. The diploid strains were used because these prevent the isolation of recessive chromosomal mutations which might give tolerance to cold stress. The strains were grown on YPD medium (2% glucose, 2% peptone, and 1% of yeast extract) or on SD medium (2% glucose, 0.7% yeast nitrogen base (Difco) without amino acids, 50 mM MES [2-(N-morpholino)-ethanesulfonic acid] adjusted to pH 5.5 with Tris, and the required amino acids, purine and pyrimidine bases).

In a first step, the sensitivity to cold of the WT diploid strain was compared with that of the gpd1 mutant strain. It was assumed that the production of glycerol could be a response against cold stress. Growth was monitored under cold stress conditions. Yeast strains were grown until stationary phase and 20 μl of 1/10, 1/100 and 1/1000 dilutions of the culture were spot on both YPD and on SD medium at a temperature of 15 or 10° C. for 10 to 14 days, and at 30° C. for 2 days as a control. 10° C. was the lowest temperature measured that allowed growth of the WT strain. Surprisingly, the gpd1 strain was shown to be cold tolerant whereas the wild type was cold sensitive (FIG. 1). This allowed the use of the WT strain for screening genes that could confer cold tolerance, while the gpd1 strain could serve as a standard cold tolerant yeast strain for comparative studies.

In a second step, the best conditions for transformation were determined. At the end the best protocol was: 300 ml YPD medium was inoculated with 30 μl of a saturated pre-culture of WT cells. The culture was grown overnight until an OD$_{660}$≈0.8, and centrifuged at 2000 rpm. The cells were subsequently washed with water and AcLiTE solution (0.1 M lithium acetate, 10 mM Tris-HCl pH 7.6 and 1 mM EDTA (Ethylene diaminetetraacetic acid, disodium salt)). Next, the pellet of cells was resuspended in 2 ml of AcLiTE solution, incubated during 15 minutes at 30° C. while shaking, whereafter 200 μl of ssDNA (10 mg/ml) was added. The cell suspension was divided in 110 μl aliquots in an Eppendorf tubes, and 200 ng of cDNA library was added. The heat shock transformation according to Gietz et al. (Nucleic Acids Res. 20, 1425, 1992) was used: in brief, 500 μl of PEG-AcLiTE solution (AcLiTE solution with 40% w/w of PEG (Polyethyleneglycol) 4000) was added to each aliquot. After mixing, the aliquots were incubated for 30 minutes at 30° C. and next for twenty minutes at 42° C.; then the cells were harvested and resuspended in 200 μl of 1M sorbitol. Two aliquots were plated in 14 cm Petri dishes with SD agar and all the necessary supplements except tryptophan (marker for the gpd1 mutation), and uracil (marker for the plasmid). To quantify the efficiency of the transformation, four 55 μl aliquots were kept separately from the original cell pellet and were inoculated with 0, 10, 50 and 100 ng of cDNA library. Then the same transformation protocol was applied, at the end the cells were resuspended in 100 μl of sorbitol and plated in 7 cm Petri dish containing the same SD medium. The average yield was about 60 colonies per ng of cDNA. In addition it was observed that transformation with competent cells that had been frozen, or transformation in one large-scale reaction instead of many small-scale reactions dramatically decreased the yield of the transformation.

Example 3

Isolation of CRYO Genes

The cDNA library constructed in pYPGE15 was used to transform the yeast WT strain W303 by the LiCl method (Nucleic Acids Res. 20, 1425, 1992). Transformants were selected on SD plates with leucine and adenine by uracil prototrophy. Three days after transformation colonies appeared in the Petri dishes. The colonies were harvested in sterile water and the number of cells quantified by plating different dilutions. On average a 10-fold higher concentration of cells than recovered from the transformation plates was plated on YPD and SD medium. Then the plates were left in a 10° C. incubator and colonies able to grow after eight days were selected. Next the tolerance of the colonies isolated in the first round was re-checked and those not giving significant tolerance were discarded. From the remaining colonies, the plasmid was eliminated by selection in minimal medium for analysing whether the tolerance was dependent on the plasmid. As a final confirmation, the plasmid was recovered from the colonies that were able to pass the previous controls, transformed into a wild type strain and again a selection for those clones giving tolerance was performed. The results obtained are summarised in Table 1:

TABLE 1

Summary of the screening procedure for the selection of cold tolerant yeast transformants on YPD or SD medium.

| | Number of colonies (YPD) | Number of colonies (SD) |
|---|---|---|
| Transformants | ≈254000 | ≈254000 |
| 1$^{rst}$ round isolated | 68 | 17 |
| Positives confirmed by retransformation | 16 | 5 |

The reconfirmed positive clones were sequenced and it was shown that they encoded different genes, among those were the genes named CRYO1, CRYO2, CRYO3, CRYO4 and CRYO5 (for cryo-tolerant). An overview is given in Table 2:

TABLE 2

| Clone | Independent isolations | Highest degree of homology to: |
|---|---|---|
| CRYO1 | 8 | *Arabidopsis thaliana* (At) protein of unknown function. DID1 (SNF7) from yeast. |
| CRYO2 | 2 | At protein of unknown function. Isoform of CRYO1. |
| CRYO3 | 4 | At protein of unknown function. DID2 from yeast. |
| CRYO4 | 1 | Yeast SEC14 |
| CRYO5 | 1 | Ring finger domain protein |

The genes encoding CRYO1 to CRYO5 proteins conferred cold stress tolerance when transferred into yeast (FIG. 2).

CRYO1 was found to be homologous to the yeast DID1 protein and, upon further analysis of the homology data, was shown to have significant homology (<90%) to the *Arabidopsis thaliana* putative proteins gi/15233464 and gi/15224854 (shown in FIG. 3). According to the invention, these putative *Arabidopsis* proteins were named AtCRYO1 and AtCRYO2 respectively.

CRYO3 is also conserved in *Arabidopsis*, with three putative proteins annotated in the database as At1g73030, At1g17730 and At4g17680, sharing more than 90% of homology. According to the invention, these putative *Arabidopsis* proteins were named AtCRYO3, AtCRYO3.2 and AtCRYO3.3 respectively. CRYO3 is also conserved in humans and mice, as shown in the pile-up of FIG. 4.

Example 4

Southern Blotting Reveals More than One Isoform in Sugar Beet

In order to confirm the presence of CRYO1 and CRYO2 in the sugar beet genome and to estimate the number of genes encoding the haemoglobin in this plant species, a Southern blot analysis was performed. Genomic DNA was prepared from leaves of 3-week old sugar beet leaves (Rogers S O and Bendich A J, Extraction of total cellular DNA from plants, algae and fungi (Eds) Plant molecular biology manual, Kluwer Academic Publishers, Dordrecht, Netherlands, 1994). 5 mg of DNA were digested with BamHI, HindIII or EcoRI, electrophoresed in 0.8% agarose gel and blotted onto a nylon membrane filter (Hybond N+, Amersham Life Science). The membrane filter was hybridised with $^{32}$P-labelled probes for CRYO1 and CRYO2. Hybridisation and washes were carried out under high stringency conditions (65° C.) (Church GM and Gilbert W., Proc. Nat. Acad. Sci. USA 81, 1991-1995, 1984). The presence of several hybridisation fragments in all lanes, independent of the restriction endonucleases used to digest the genomic DNA, suggests that there are several isoforms in the genome, especially for CRYO2 (FIG. 5).

Example 5

CRYO2 is not Induced by NaCl and ABA in Sugar Beet

Figure 6:
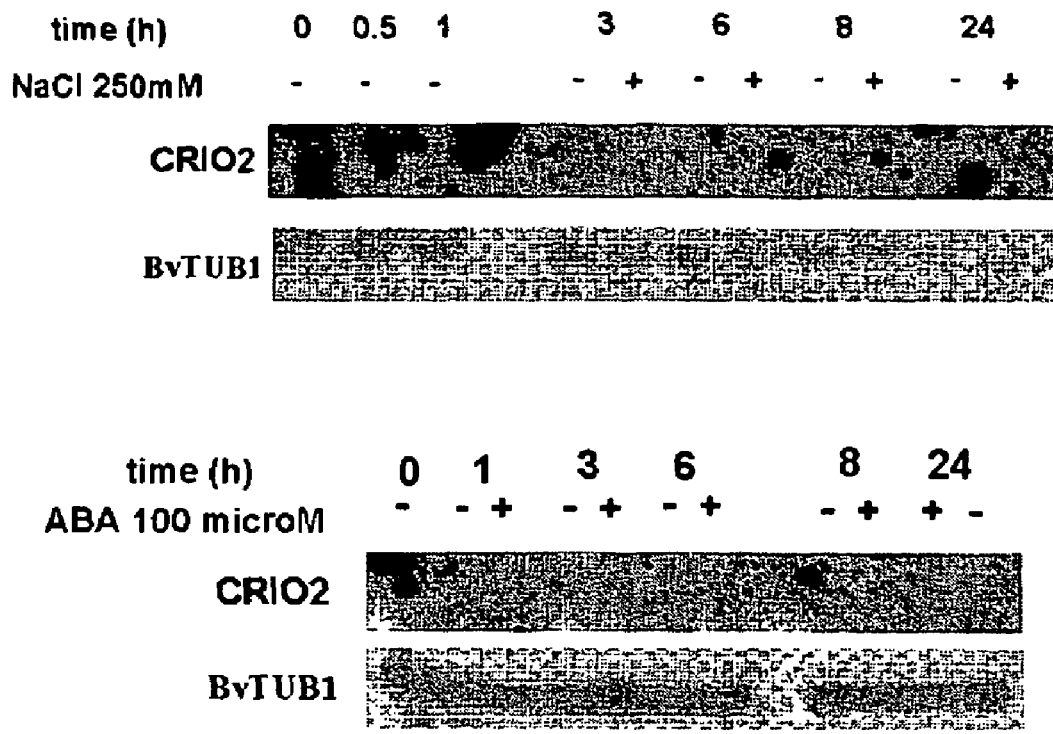
FIG. 6: a) Northern blot with a CRYO2 probe. Different timepoints (in hrs) after treating the sugar beet plants with 250 mM NaCl are indicated. $\alpha_3$-tubulin was used as control. b) Northern blot with a CRYO2 probe. Different timepoints (in hrs) after treating the sugar beet plants with 100 μM ABA are indicated. α₃-tubulin was used as control.

In order to investigate whether CRYO2 also participates in the response of sugar beet plants to salt stress, the accumulation of CRYO2 mRNA in response to various exposure times to NaCl was analysed using northern blot analysis. Total RNA was isolated from control, 250 mM Na$^+$ or 100 mM ABA-treated sugar beet leaves as described by Davis et al. (Basic methods in Molecular Biology. Elsevier. Amsterdam pp. 143-146 1986). 30 mg of total RNA were separated on a 1% agarose gel containing 2.2% formaldehyde and blotted onto a nylon membrane filter (Hybond N, Amersham Life Science). Hybridization using the above described probe. The CRYO2 specific probe showed only one band that corresponded to the size of the CRYO2 cDNA. The filter was washed twice with 4×SSC buffer (0.6 M NaCl, 0.06 M trisodium citrate adjusted to pH 7 with HCl), 0.1% SDS for 5 minutes and twice with 0.4×SSC, 0.1% SDS for five minutes at 65° C. The same filter was re-hybridized with a 1.9 kb EcoRI fragment comprising the $\alpha_3$-tubulin gene of *Arabidopsis thaliana* (Ludwig et al., PNAS 84, 5833-5837, 1987). As shown in FIG. 6a the CRYO2 mRNA did not accumulate with time upon NaCl treatment. Similarly, no induction of CRYO2 after 3 hours of ABA treatment was observed (FIG. 6b).

Example 6

CRYO5 Gives Also Tolerance to Oxidative Stress

A dilution series of W303 pYPGECRYO5 and wt yeast (control) was plated on YPD medium with 1 mM tert-butyl hydroperoxyde (t-BOOH) and tested for tolerance to oxidative stress after 2 and 4 days.

Figure 7:
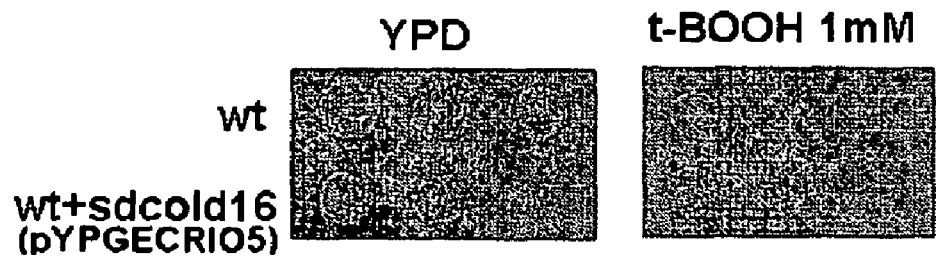
FIG. 7: Growth of wild type yeast (upper row) and yeast transformed with the CRYO5 gene (bottom row) on YPD (left panel) and YPD supplemented with 1 mM tert-butyl hydroperoxide (right panel).

The yeast clone with CRYO5 had a strong t-BOOH tolerance phenotype and the phenotype was very reproducible: at a concentration of 1 mM t-BOOH, control yeast cells did not grow at all, whilst yeast cells overexpressing CRYO5 did (FIG. 7).

The definition of a strong phenotype is based on drop test experiments. Different dilutions of saturated cultures (1:10, 1:100, 1:1000) were made and these were grown on selective media (YPD with 1 mM t-BOOH). "Strong phenotypes" were those clones that grew well in all the dilutions assayed. With "no strong phenotypes" is meant that the clone does not grow in all dilutions. The control cells expressing the empty plasmid did not grow at all in the selective media.

Example 7

Construction of Cold Tolerant Plants

Plants are transformed with at least one of the CRYO genes in an expressible format under control of a constitutive or inducible promoter, using standard techniques.

Example 8

Testing of Cold Tolerant Plants

Transformed plants are tested by subjecting the plants to cold stress during a sufficiently long time period. When compared to the same untransformed plant line, the transformed lines show a better growth during stress conditions and/or better recovery after stress conditions and/or higher yield (biomass and/or harvestable parts).

The invention claimed is:

1. An isolated protein comprising the sequence shown in SEQ ID NO: 4.

2. An isolated protein consisting of the sequence shown in SEQ ID NO: 4.

3. An isolated variant of a protein comprising the amino acid shown in SEQ ID NO:4, wherein the variant comprises an amino acid sequence that is at least 95% identical to SEQ ID NO:4, said variant being capable of increasing stress tolerance of a yeast cell.

4. The isolated variant protein of claim 3 wherein the variant comprises an amino acid sequence that is at least 96% identical to SEQ ID NO:4.

5. The isolated variant protein of claim 3 wherein the variant comprises an amino acid sequence that is at least 97% identical to SEQ ID NO:4.

6. The isolated variant protein of claim 3 wherein the variant comprises an amino acid sequence that is at least 98% identical to SEQ ID NO:4.

7. The isolated variant protein of claim 3 wherein the variant comprises an amino acid sequence that is at least 99% identical to SEQ ID NO:4.

8. A method of increasing abiotic stress tolerance in yeast comprising transforming yeast with a nucleic acid sequence encoding a protein of claim 1, and expressing the protein of claim 1 in said yeast such that said yeast demonstrate increased abiotic stress tolerance as compared with control yeast.

9. A method of increasing abiotic stress tolerance in yeast comprising transforming yeast with a nucleic acid sequence encoding a protein of claim 1, and expressing the protein of claim 2 in said yeast such that said yeast demonstrate increased abiotic stress tolerance as compared with control yeast.

10. The method of claim 8 wherein said abiotic stress is temperature stress.

11. The method of claim 9 wherein said abiotic stress is temperature stress.

12. The method of claim 8 wherein said abiotic stress is cold temperature stress.

13. The method of claim 9 wherein said abiotic stress is cold temperature stress.

* * * * *

UNITED STATES PATENT AND TRADEMARK OFFICE
CERTIFICATE OF CORRECTION

PATENT NO. : 7,612,177 B2 Page 1 of 1
APPLICATION NO. : 10/552686
DATED : November 3, 2009
INVENTOR(S) : Mulet Salort et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 635 days.

Signed and Sealed this

Nineteenth Day of October, 2010

David J. Kappos
*Director of the United States Patent and Trademark Office*

SEQUENCE LISTING

<160> NUMBER OF SEQ ID NOS: 10

<210> SEQ ID NO 1
<211> LENGTH: 1344
<212> TYPE: DNA
<213> ORGANISM: Beta vulgaris
<220> FEATURE:
<221> NAME/KEY: misc_feature
<222> LOCATION: (3)..(3)
<223> OTHER INFORMATION: n is a, c, g, or t

<400> SEQUENCE: 1

```
cgnctgcagg aattcggcac gagtttcgaa gtacccaaga ctccaagaga ggacgaactt      60
cagtttctct ctcctcgaaa tcctaattct ctctgctcaa atccctaatt ctctctcctc     120
acgatcgtag agtctctgtt tttcactgta taaatctatt caaacaattt tctctctcct     180
attatttcaa tttcggtttg ctaattcaag gtgaatcaaa tgtcggcaaa tatgttttcc     240
agactttttg gtgctaaatc tcgtgatgca gctactactg agactacttt atctacatta     300
gagaaattga atgagacact tgaaatgcta gagaagaaag agcagcttct aatgaaaaag     360
gctactgcag aggttgaaaa ggccaaagag ttcacaaggg caagaataaa cgtgctgct      420
atacaatgtt taagaggaa aaggttatac gaacagcaag tcgagcaggt tgggaatttt     480
caactacgaa ttcatgatca gatcataatg cttgattctg caaaagcaac gacagagaca     540
gttgctgcat tgagatctgg tgctagtgct atgaaggcta tgcagaaagc aacaaacatt     600
gatgatgtgg acaagacaat ggatgagatc aatgagcaga ccgataactt gagacagata     660
caggaggcac tagctactcc tgttggtgca actgattttg atgaggatga attggaagct     720
gagcttgaag aacttgaagg agctgagttg gaggaacaac ttctacaacc atttacaact     780
gccctacgg caccaattca tgttccagaa ggcaagctgc cagcaaggcc aacaccccaa     840
aagaactctg aggaagatga actcgctgcg ttacaagcag aaatggcact tgaaggctt      900
ttctttttc atgtttataa tcatgtccca agaaatgga acgggctgg aaaaaggaaa        960
aggcaaagga aaagaaaagg aaaagaaaaa gattgaaaat ctttattgat tgatggtggt    1020
atatttaagt attgagtgtt gatagcatct tgttgtcatg tactatatgc ctatatggag    1080
tacctgttat taattggtaa tgttaatgca aatattgtct ataccattga tgaacaaaga    1140
tgggggctgt aaactcttgg ttgttttttc gttttcaat ttttttgttt cgttttatt    1200
tttcagtcac ctactggttc tagtgactgg tgacaattgc tgtacagaga ttttgttgca    1260
cttgagctgc tggtcaacag actatgcaga ctgtcagatt tataaaatca gaaagctggc    1320
aaaaaaaaaa aaaaaaaact cgag                                           1344
```

<210> SEQ ID NO 2
<211> LENGTH: 224
<212> TYPE: PRT
<213> ORGANISM: Beta vulgaris

<400> SEQUENCE: 2

```
Met Ser Ala Asn Met Phe Ser Arg Leu Phe Gly Ala Lys Ser Arg Asp
  1               5                  10                  15

Ala Ala Thr Thr Glu Thr Thr Leu Ser Thr Leu Glu Lys Leu Asn Glu
             20                  25                  30

Thr Leu Glu Met Leu Glu Lys Lys Glu Gln Leu Leu Met Lys Lys Ala
         35                  40                  45
```

```
Thr Ala Glu Val Glu Lys Ala Lys Glu Phe Thr Arg Ala Lys Asn Lys
 50                  55                  60

Arg Ala Ala Ile Gln Cys Leu Lys Arg Lys Arg Leu Tyr Glu Gln Gln
 65                  70                  75                  80

Val Glu Gln Val Gly Asn Phe Gln Leu Arg Ile His Asp Gln Ile Ile
                 85                  90                  95

Met Leu Asp Ser Ala Lys Ala Thr Thr Glu Thr Val Ala Ala Leu Arg
                100                 105                 110

Ser Gly Ala Ser Ala Met Lys Ala Met Gln Lys Ala Thr Asn Ile Asp
            115                 120                 125

Asp Val Asp Lys Thr Met Asp Glu Ile Asn Glu Gln Thr Asp Asn Leu
130                 135                 140

Arg Gln Ile Gln Glu Ala Leu Ala Thr Pro Val Gly Ala Thr Asp Phe
145                 150                 155                 160

Asp Glu Asp Glu Leu Glu Ala Glu Leu Glu Glu Leu Glu Gly Ala Glu
                165                 170                 175

Leu Glu Glu Gln Leu Leu Gln Pro Phe Thr Thr Ala Pro Thr Ala Pro
            180                 185                 190

Ile His Val Pro Glu Gly Lys Leu Pro Ala Arg Pro Thr Pro Gln Lys
        195                 200                 205

Asn Ser Glu Glu Asp Glu Leu Ala Ala Leu Gln Ala Glu Met Ala Leu
    210                 215                 220
```

<210> SEQ ID NO 3
<211> LENGTH: 1341
<212> TYPE: DNA
<213> ORGANISM: Beta vulgaris
<220> FEATURE:
<221> NAME/KEY: misc_feature
<222> LOCATION: (934)..(934)
<223> OTHER INFORMATION: n is a, c, g, or t

<400> SEQUENCE: 3

```
cccgcctgca ggaattcggc acgagagaaa acctgtctta tacttctcta ctttgctttt      60
ttgttttggt tagccaacca atctaaccca gaattgataa tcccactctt caattccctc     120
aaaattttc ttccaaaatt catttccact attttcagat atttcatcac taaaatctcc     180
tcgagttaac ctaatcactc cattcttatt tcctctcgga aaaaaaccta atcaatcaac     240
tttacgcggt tcattctcc gatcttttc gtttcctcgt aatttttag cgatcaccca       300
ttttcgttaa atatgttac aagggttttc ggtaaaccta aggaaggaac aacgagtgct      360
gttgcaacgt tagacaaatt gagtgagaca ctcgaaatgt tggaaaaaaa agaacaggtg     420
cttttgaaga aggctggtgc tgaggttgaa aaggccaagg agttcactag agcaaagaac     480
aaacgtgctg ctataacttg tctgaagagg aagaggctat acgaacaaca aatagagcag     540
cttggaaaca tgcagttgcg aattcatgat cagatgatac tgcttgaagg ggcaaaggca     600
acaacagaga ctgtcgatgc attgaggtct ggtgcctcgg ctatgaaggc catgcaaaag     660
gcaacaaaca tcgataatgt ggataaaact atggacgaga tcaatgagca gacagagaac     720
ttaaaacaaa tacaggaagc tctctctgct ccaatcggtg cagcagctga cttttgatga     780
ggatgacctg aaagcagagc ttgaagagct agaaggtgct gaattgaaga gcaacttat      840
cagcccagct actactgctc ctgctgcacc agtgcatgct cctgctggaa aacaacctga     900
cgcccctgca cctcgggaag aatactgctt gaanaggatg agctcgccgc gttgcaagca     960
gagatggccc ctgtaaaaag ttttctcgga ctggaataca ggagttggtc ttacatcaaa    1020
```

```
gtagctgtat aataagctaa ttattattgc tttgggtacc acctttacag gcacgtatta    1080
cccaatcacg gatatttggt aataaaatgt gctgtgtagg ttgcgtgatg ttgttgatta    1140
ggccgtagtt ctccttgtgc caggtcttga ttgcacctta ttctcgatgt aaatttcaga    1200
ttctcttata gacattgtaa tttgtgacaa aatatcgatc atttggtacg agttaaccct    1260
tcacatatgt aaaagaaata aaatacaatt cttgtatgac tttattttaa ccaaaaaaaa    1320
aaaaaaaaaa aactcgaggg g                                              1341

<210> SEQ ID NO 4
<211> LENGTH: 154
<212> TYPE: PRT
<213> ORGANISM: Beta vulgaris

<400> SEQUENCE: 4

Met Phe Thr Arg Val Phe Gly Lys Pro Lys Glu Gly Thr Thr Ser Ala
1               5                   10                  15

Val Ala Thr Leu Asp Lys Leu Ser Glu Thr Leu Glu Met Leu Glu Lys
            20                  25                  30

Lys Glu Gln Val Leu Leu Lys Lys Ala Gly Ala Glu Val Glu Lys Ala
        35                  40                  45

Lys Glu Phe Thr Arg Ala Lys Asn Lys Arg Ala Ala Ile Thr Cys Leu
    50                  55                  60

Lys Arg Lys Arg Leu Tyr Glu Gln Gln Ile Glu Gln Leu Gly Asn Met
65                  70                  75                  80

Gln Leu Arg Ile His Asp Gln Met Ile Leu Leu Glu Gly Ala Lys Ala
                85                  90                  95

Thr Thr Glu Thr Val Asp Ala Leu Arg Ser Gly Ala Ser Ala Met Lys
            100                 105                 110

Ala Met Gln Lys Ala Thr Asn Ile Asp Asn Val Asp Lys Thr Met Asp
        115                 120                 125

Glu Ile Asn Glu Gln Thr Glu Asn Leu Lys Gln Ile Gln Glu Ala Leu
    130                 135                 140

Ser Ala Pro Ile Gly Ala Ala Ala Asp Phe
145                 150

<210> SEQ ID NO 5
<211> LENGTH: 1019
<212> TYPE: DNA
<213> ORGANISM: Beta vulgaris
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t

<400> SEQUENCE: 5
cccgnctgca ggaattcggc acgagcgatc tccccaattc tccttctctc aaagatggga     60
aacaccgaga aactaatgaa ccagatcatg gagctcaaat tcacctctaa atcacttcaa    120
cgtcaatctc gtaagtgcga gaaagaagaa aaagctgaga aactcaaagt caagaaagca    180
atcgagaaag gaaacatgga tggagctcga atttacgccg aaaacgcaat tcgtaagcgt    240
actgaacaga tgaactactt gcgcctcgct tctcgcctcg acgccgtcgt ttcgcgcctc    300
gatactcaag ctaagatgca aaccatcgga aaatcgatgg gatcaattgt taaatcgctt    360
gagtcgtctt tgaataccgg taatttgcag aagatgtcgg agacaatgga caattttgag    420
```

-continued

```
aagcaatttg ttaatatgga agttcaggct gagtttatgg agagttctat ggctgggagt    480
acttcgcttt cgactcccga aaccgaggtt aatagtttga tgcagcaggt ggcggatgat    540
tatggccttg aggtttctgt gggtttgcct caggctgctg acatgctat tcctgttccg     600 aaggcggcgg agaaggttga tgaggatgat cttaccagga ggctcgccga gctcaaggct    660
cgaggttgaa gtcaaggta aaaggttaa ggttttattg ataatgttgt atagattatg      720
agctttactg atgatcaacc cttcgtgata tgggggtttg atgataattt gctctatatt    780
atggagattt ggagcttttg gaaccgataa ctgtggatgg tttaattatg tattatattg    840
tatttgtcta ttgaaaaaa aaaaaaaaa aaaactcgag gggggccccg gtaccaagat      900
ggcctttggt gggttgaaga aggaaaaaga cagaaacgac ttaattacct acttgaaaaa    960
agcctgtgag taaacaggcc cctttccctt tgtcgatatc ntgtaattag ttaggggggt    1019
```

<210> SEQ ID NO 6
<211> LENGTH: 204
<212> TYPE: PRT
<213> ORGANISM: Beta vulgaris

<400> SEQUENCE: 6

```
Met Gly Asn Thr Glu Lys Leu Met Asn Gln Ile Met Glu Leu Lys Phe
1               5                   10                  15

Thr Ser Lys Ser Leu Gln Arg Gln Ser Arg Lys Cys Glu Lys Glu Glu
            20                  25                  30

Lys Ala Glu Lys Leu Lys Val Lys Ala Ile Glu Lys Gly Asn Met
        35                  40                  45

Asp Gly Ala Arg Ile Tyr Ala Glu Asn Ala Ile Arg Lys Arg Thr Glu
    50                  55                  60

Gln Met Asn Tyr Leu Arg Leu Ala Ser Arg Leu Asp Ala Val Val Ser
65                  70                  75                  80

Arg Leu Asp Thr Gln Ala Lys Met Gln Thr Ile Gly Lys Ser Met Gly
                85                  90                  95

Ser Ile Val Lys Ser Leu Glu Ser Ser Leu Asn Thr Gly Asn Leu Gln
            100                 105                 110

Lys Met Ser Glu Thr Met Asp Asn Phe Glu Lys Gln Phe Val Asn Met
        115                 120                 125

Glu Val Gln Ala Glu Phe Met Glu Ser Ser Met Ala Gly Ser Thr Ser
    130                 135                 140

Leu Ser Thr Pro Glu Thr Glu Val Asn Ser Leu Met Gln Gln Val Ala
145                 150                 155                 160

Asp Asp Tyr Gly Leu Glu Val Ser Val Gly Leu Pro Gln Ala Ala Gly
                165                 170                 175

His Ala Ile Pro Val Pro Lys Ala Ala Glu Lys Val Asp Glu Asp Asp
            180                 185                 190

Leu Thr Arg Arg Leu Ala Glu Leu Lys Ala Arg Gly
        195                 200
```

<210> SEQ ID NO 7
<211> LENGTH: 1510
<212> TYPE: DNA
<213> ORGANISM: Beta vulgaris
<220> FEATURE:
<221> NAME/KEY: misc_feature
<222> LOCATION: (2)..(3)
<223> OTHER INFORMATION: n is a, c, g, or t -continued

```
<400> SEQUENCE: 7
tnncccgggc tgcaggaatt cggcacgagc tcatttctct acatcaaaaa cacaacaaag      60
agatcaccca tggcggaaga aacccataag ccagaatcaa cggtggctga agtggtggtt     120
ccagtagccg agaaaccagc tgagaagcca gctgagaagg cagttctacc acctgaagct     180
gagaaactag ctgcagctga atcagctgaa gccgagaagc cagctgattc agccgaggct     240
aagatagctc aacaagtctc attcaaagag gagactaatg ttgcaagtga gctacctgag     300
ctacatagaa aggctctcga ggacttgaag aaacttattc aagaagccct cgagaagcac     360
gagttctctt ctcctcctcc tccgcctccg cctgctccag ctaaagttga ggagaaggcg     420
gaagagaaga aagaggaaca acctccatcc accacctcca ccaccaccac caccaccacc     480
gcggtttcag atgaggttgc tgttgctcct ccatccgaag aggccccgaa aactgacgag     540
gcctctccga agtggagga ggagcctgca aaatagttg agcaaccacc tacaacaccg      600
gcagaagaac ctgaaccagc aaaaacacct gaggttgttg ttgctgaaga ggagaaaact     660
ggtgaggata ttaagaaac tatagtagtc gaggttgcga caactacagc agcaccagta     720
ctaacgaaac cagaatctgt tgaggagaca ccaaaagaag ctgaagttgt agtggaagaa     780
tcaccaaagg agccagaaga agtatcaata tggggaattc cacttcttgc tgatgaaaga     840
agtgatgtaa ttctattgaa attcttaaga gcaagagatt atagagtgaa agatgctttc     900
actatgatta gaaatactgc tcgttggaga aaagaatttg aggttgattc tttacttgat     960
gaagatcttg gaaatgatta tgagaaagtt gttttacac atggagttga taaacaaggt    1020
cgtcctgttt gttataatgt gtttggagag tttcaaaata aggaacttta tcagaatact    1080
ttctctgatg cagaaaaaag gaaaaagttc ttgagatggt tgattcaatt ccttgaaaaa    1140
actattagaa ctcttgattt tagtcctgaa ggaattaatt cttttgttct tgttaatgat    1200
ttgaagaatt ctcctgggta tggtaagaga gatctttaca aagttattga caagtttctt    1260
gagattctcc aggataatta cccagaattt gctgctaaac agttgtgcat caatgtttca    1320
tggtggtctt ggcatacaac tggatctatt tgactgtatt tacaccaagg agcaagagca    1380
agtttgtgtt tgcaagccca tctaaaactg ctgagaccct tttcaagtac atagctcctg    1440
agcaggtgcc tgttcaattt ggtgggcaca gcaagtttgg cgagcatgag ttttcccctg    1500
ctgatactgt                                                           1510

<210> SEQ ID NO 8
<211> LENGTH: 427
<212> TYPE: PRT
<213> ORGANISM: Beta vulgaris

<400> SEQUENCE: 8

Met Ala Glu Glu Thr His Lys Pro Glu Ser Thr Val Ala Glu Val Val
1               5                  10                  15

Val Pro Val Ala Glu Lys Pro Ala Glu Lys Pro Ala Glu Lys Ala Val
                20                  25                  30

Leu Pro Pro Glu Ala Glu Lys Leu Ala Ala Ala Glu Ser Ala Glu Ala
            35                  40                  45

Glu Lys Pro Ala Asp Ser Ala Glu Ala Lys Ile Ala Gln Gln Val Ser
        50                  55                  60

Phe Lys Glu Glu Thr Asn Val Ala Ser Glu Leu Pro Glu Leu His Arg
65                  70                  75                  80

Lys Ala Leu Glu Asp Leu Lys Lys Leu Ile Gln Glu Ala Leu Glu Lys
                85                  90                  95
```

```
His Glu Phe Ser Ser Pro Pro Pro Pro Pro Ala Pro Ala Lys
            100                 105                 110
Val Glu Glu Lys Ala Glu Glu Lys Lys Glu Glu Gln Pro Pro Ser Thr
        115                 120                 125
Thr Ser Thr Thr Thr Thr Thr Thr Thr Ala Val Ser Asp Glu Val Ala
    130                 135                 140
Val Ala Pro Pro Ser Glu Glu Ala Pro Lys Thr Asp Glu Ala Ser Pro
145                 150                 155                 160
Lys Val Glu Glu Glu Pro Ala Lys Ile Val Glu Gln Pro Pro Thr Thr
                165                 170                 175
Pro Ala Glu Glu Pro Glu Pro Ala Lys Thr Pro Glu Val Val Val Ala
            180                 185                 190
Glu Glu Glu Lys Thr Gly Glu Asp Ile Lys Glu Thr Ile Val Val Glu
        195                 200                 205
Val Ala Thr Thr Thr Ala Ala Pro Val Leu Thr Glu Pro Glu Ser Val
    210                 215                 220
Glu Glu Thr Pro Lys Glu Ala Glu Val Val Glu Glu Ser Pro Lys
225                 230                 235                 240
Glu Pro Glu Glu Val Ser Ile Trp Gly Ile Pro Leu Leu Ala Asp Glu
                245                 250                 255
Arg Ser Asp Val Ile Leu Leu Lys Phe Leu Arg Ala Arg Asp Tyr Arg
            260                 265                 270
Val Lys Asp Ala Phe Thr Met Ile Arg Asn Thr Ala Arg Trp Arg Lys
        275                 280                 285
Glu Phe Glu Val Asp Ser Leu Leu Asp Glu Asp Leu Gly Asn Asp Tyr
    290                 295                 300
Glu Lys Val Val Phe Thr His Gly Val Asp Lys Gln Gly Arg Pro Val
305                 310                 315                 320
Cys Tyr Asn Val Phe Gly Glu Phe Gln Asn Lys Glu Leu Tyr Gln Asn
                325                 330                 335
Thr Phe Ser Asp Ala Glu Lys Arg Lys Lys Phe Leu Arg Trp Leu Ile
            340                 345                 350
Gln Phe Leu Glu Lys Thr Ile Arg Thr Leu Asp Phe Ser Pro Glu Gly
        355                 360                 365
Ile Asn Ser Phe Val Leu Val Asn Asp Leu Lys Asn Ser Pro Gly Tyr
    370                 375                 380
Gly Lys Arg Asp Leu Tyr Lys Val Ile Asp Lys Phe Leu Glu Ile Leu
385                 390                 395                 400
Gln Asp Asn Tyr Pro Glu Phe Ala Ala Lys Gln Leu Cys Ile Asn Val
                405                 410                 415
Ser Trp Trp Ser Trp His Thr Thr Gly Ser Ile
            420                 425
```

<210> SEQ ID NO 9
<211> LENGTH: 2052
<212> TYPE: DNA
<213> ORGANISM: Beta vulgaris
<220> FEATURE:
<221> NAME/KEY: misc_feature
<222> LOCATION: (2049)..(2049)
<223> OTHER INFORMATION: n is a, c, g, or t

<400> SEQUENCE: 9
cccgcctgca ggattcggca cgagcttcaa taaaggtgag agttagagag agaaagtgaa    60
ggaaggccgc ctcttttttg ggtcgctgac tattaactga aactttgtaa atctactcat   120

-continued

```
ggatgaatat tccaatagaa aatcttctgg tcttgctatc tccaggagag ggcctagcct    180
tgttttaagg gactcagcgg agaacaacaa agatcggaat gttcaggttt gcagccgagt    240
tggatgtggc agcaagttga attcagtgaa ggatgctaaa gttagctctc cgagtaaagt    300
caaatctcca aaaactcctt tccgttcatc tgctcaagga aaagaaacca ttggaagttc    360
atccagaact ctggcttctc ctagtccttt taaaaaatct ctttcagacc ggaagaaaaa    420
actgccttct aatcttgaca ctgattcaga aatgtgcagt cttcaagatg aatccgagga    480
agtctctgga aagacccgga taagggttca gcccgagcca aagatcatg attccattga    540
agcttcatca tctgaagctg ggagttccag ttcgggaccc tctaacagat ggcaaacag    600
aaatactcag aggtttgggt tggggcgcca agattctgct gcaagttctg cttcattttc    660
tttaaataaa accaaccaag ggcaaagaaa tggtggtggt ggtggtgcta gtgctaacag    720
gtataatctg cgacaattaa aatgtaactc aatctctgac gttgttccat caggttctcc    780
gcagtctgct gaatcaagtc tcagtaagaa gagggacaca ggttgtagga agagaaatgg    840
tgaagctgag agtagtttac ctgtgagagg taagaaaatt aatggggcaa cccaagatga    900
taggaggaat gactatccaa atcgtggaat atcaatatct gatacaaggc gtaccagaag    960
ctcgagtcct gggaataacg atgtcacgtc tgttaggagt cggagatctg ttgctagaac   1020
aaggctttca atcaggata cccgggatag attaccattg gttgagtcac ccctgaggaa   1080
cccatcttca cctctacccg agtcatcaac tggaggaact gatttttagtt tggaaaatca   1140
gttctctggc cgaactccag ctggttcttt aagttcttat aatagaccag gtggcggtag   1200
tgaacatatg cggcctagta ggtctattga tccctatgaa gctggcattg ctcgctcttt   1260
tatgaaccgt gataccttaa gacagtacaa cttagatggg attgcagaga tgttattagc   1320
tctagagaga attgaacaag aagaagatcc aacctatgag caattgcttg ttctggagac   1380
taatcttttc ctaggaggac tttcttttca tgatcagcac agggacatga ggctggatat   1440
tgataatatg tcatatgagg aactattagc tttagaagag agcatgggaa ctgtaagaca   1500
gccgtgccag aagatgattt ggctaagtgt cttaaaagga acatctacca gggtgttgca   1560
gattgtagag aggatgagca tgatatcaaa tgcagcatat gccaggaaga atatggtggc   1620
ggggaagaag taggaagatt gagttgtgat cacagctacc acattgaatg tataaatcaa   1680
tggttgaggc tcaagaactg gtgccctatc tgcaaggctt ctgcatcacc ttcaacttca   1740
gcaactccgc ctccctgaac ttcgctgtta tattcttccc tttttttttcc agtttgtaca   1800
gaccggaatc tgtcgatttt tatttcttca tcagaaattt gatgtttcta tagatagtcc   1860
tttggttact attttctttt tccttatttg tacatataat ttctcttcta tgtgccaact   1920
aataatgctc gagctgttag aagctccagt atgggaacag gttcacttca cttatttttac   1980
ataaacagat tctcaagtat atataaatcc ctctcctcaa aaaaaaaaa aaaaaacccg   2040
agggggggng cg                                                       2052
```

<210> SEQ ID NO 10
<211> LENGTH: 504
<212> TYPE: PRT
<213> ORGANISM: Beta vulgaris

<400> SEQUENCE: 10

```
Met Asp Glu Tyr Ser Asn Arg Lys Ser Ser Gly Leu Ala Ile Ser Arg
1               5                   10                  15
Arg Gly Pro Ser Leu Val Leu Arg Asp Ser Ala Glu Asn Asn Lys Asp
            20                  25                  30
```

-continued

```
Arg Asn Val Gln Val Cys Ser Arg Val Gly Cys Gly Ser Lys Leu Asn
    35                  40                  45
Ser Val Lys Asp Ala Lys Val Ser Ser Pro Ser Lys Val Lys Ser Pro
50                  55                  60
Lys Thr Pro Phe Arg Ser Ser Ala Gln Gly Lys Glu Thr Ile Gly Ser
65                  70                  75                  80
Ser Ser Arg Thr Leu Ala Ser Pro Ser Pro Phe Lys Lys Ser Leu Ser
                85                  90                  95
Asp Arg Lys Lys Lys Leu Pro Ser Asn Leu Asp Thr Asp Ser Glu Met
            100                 105                 110
Cys Ser Leu Gln Asp Glu Ser Glu Val Ser Gly Lys Thr Arg Ile
        115                 120                 125
Arg Val Gln Pro Glu Pro Glu Asp His Asp Ser Ile Glu Ala Ser Ser
    130                 135                 140
Ser Glu Ala Gly Ser Ser Ser Gly Pro Ser Asn Arg Leu Ala Asn
145                 150                 155                 160
Arg Asn Thr Gln Arg Phe Gly Leu Gly Arg Gln Asp Ser Ala Ala Ser
                165                 170                 175
Ser Ala Ser Phe Ser Leu Asn Lys Thr Asn Gln Gly Arg Asn Gly
            180                 185                 190
Gly Gly Gly Gly Ala Ser Ala Asn Arg Tyr Asn Leu Arg Gln Leu Lys
        195                 200                 205
Cys Asn Ser Ile Ser Asp Val Val Pro Ser Gly Ser Pro Gln Ser Ala
    210                 215                 220
Glu Ser Ser Leu Ser Lys Lys Arg Asp Thr Gly Cys Arg Lys Arg Asn
225                 230                 235                 240
Gly Glu Ala Glu Ser Ser Leu Pro Val Arg Gly Lys Lys Ile Asn Gly
                245                 250                 255
Ala Thr Gln Asp Asp Arg Arg Asn Asp Tyr Pro Asn Arg Gly Ile Ser
            260                 265                 270
Ile Ser Asp Thr Arg Arg Thr Arg Ser Ser Pro Gly Asn Asn Asp
        275                 280                 285
Val Thr Ser Val Arg Ser Arg Arg Ser Val Ala Arg Thr Arg Leu Ser
    290                 295                 300
Asn Gln Asp Thr Arg Asp Arg Leu Pro Leu Val Glu Ser Pro Leu Arg
305                 310                 315                 320
Asn Pro Ser Ser Pro Leu Pro Glu Ser Ser Thr Gly Gly Thr Asp Phe
                325                 330                 335
Ser Leu Glu Asn Gln Phe Ser Gly Arg Thr Pro Ala Gly Ser Leu Ser
            340                 345                 350
Ser Tyr Asn Arg Pro Gly Gly Gly Ser Glu His Met Arg Pro Ser Arg
        355                 360                 365
Ser Ile Asp Pro Tyr Glu Ala Gly Ile Ala Arg Ser Phe Met Asn Arg
    370                 375                 380
Asp Thr Leu Arg Gln Tyr Asn Leu Asp Gly Ile Ala Glu Met Leu Leu
385                 390                 395                 400
Ala Leu Glu Arg Ile Glu Gln Glu Glu Asp Pro Thr Tyr Glu Gln Leu
                405                 410                 415
Leu Val Leu Glu Thr Asn Leu Phe Leu Gly Gly Leu Ser Phe His Asp
            420                 425                 430
Gln His Arg Asp Met Arg Leu Asp Ile Asp Asn Met Ser Tyr Glu Glu
        435                 440                 445
```

-continued

```
Leu Leu Ala Leu Glu Glu Ser Met Gly Thr Val Arg Gln Pro Cys Gln
    450                 455                 460

Lys Met Ile Trp Leu Ser Val Leu Lys Gly Thr Ser Thr Arg Val Leu
465                 470                 475                 480

Gln Ile Val Glu Arg Met Ser Met Ile Ser Asn Ala Ala Tyr Ala Arg
                485                 490                 495

Lys Asn Met Val Ala Gly Lys Lys
                500
```